United States Patent
Mazlouman et al.

(10) Patent No.: US 9,590,583 B2
(45) Date of Patent: Mar. 7, 2017

(54) ALTERNATING CURRENT (AC) COUPLER FOR WIDEBAND AC SIGNALS AND RELATED METHODS

(71) Applicant: Agilent Technologies, Inc., Santa Clara, CA (US)

(72) Inventors: Shahrzad Jalali Mazlouman, Bellevue, WA (US); David Deford, Pleasanton, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 0 days.

(21) Appl. No.: 14/753,958

(22) Filed: Jun. 29, 2015

(65) Prior Publication Data
US 2016/0380609 A1     Dec. 29, 2016

(51) Int. Cl.
*H01P 3/08*      (2006.01)
*H03H 7/38*     (2006.01)
(Continued)

(52) U.S. Cl.
CPC ........... *H03H 7/383* (2013.01); *G01N 27/622* (2013.01); *H01J 49/40* (2013.01); *H01P 3/08* (2013.01);
(Continued)

(58) Field of Classification Search
CPC ... H01L 2223/6627; H01L 2924/19032; H01P 3/06; H01P 3/08; H01P 3/081; H01P 3/088
(Continued)

(56) References Cited

U.S. PATENT DOCUMENTS 6,515,561 B2 * 2/2003 Tamura .................... H01P 1/047
                                                          333/219
7,046,100 B2 * 5/2006 Yagisawa .............. H01P 1/2013
                                                          333/24 C
(Continued)

FOREIGN PATENT DOCUMENTS

WO      2014066872 A2     5/2014

OTHER PUBLICATIONS

MagneTOF: A New Class of Robust Sub-nanosecond TOF Detectors with Exceptional Dynamic Range; ETP electron multipliers, SGE Publication No. PD-0257-A. Rev:00 05-06 (2006).
(Continued)

*Primary Examiner* — Dean Takaoka
*Assistant Examiner* — Alan Wong

(57) ABSTRACT

An AC coupler for transmitting high-frequency components of a wideband signal includes a signal conductor and a shielding structure arranged as a transmission line. The signal conductor includes a conductive element and a capacitor configured to block direct current (DC) components of the wideband signal while transmitting high-frequency alternating current (AC) components of the wideband signal. The shielding structure is configured for conducting at least the AC components of the wideband signal while confining electric fields and currents in the shielding structure substantially to a region proximate to the signal conductor. The shielding structure has a width substantially greater than a width of the signal conductor. The difference between the shielding structure width and the signal conductor width may be substantially greater than an offset distance between the signal conductor and the shielding structure.

20 Claims, 17 Drawing Sheets

(51) Int. Cl.
*H01J 49/40* (2006.01)
*G01N 27/62* (2006.01)
*H03H 7/00* (2006.01)
*H03H 7/01* (2006.01)
*H01P 11/00* (2006.01)

(52) U.S. Cl.
CPC ........... *H01P 11/001* (2013.01); *H03H 7/004* (2013.01); *H03H 7/0123* (2013.01); *H03H 7/0138* (2013.01)

(58) Field of Classification Search
USPC ...... 333/24 R, 156, 157, 160, 161, 245, 246
See application file for complete search history.

(56) References Cited

U.S. PATENT DOCUMENTS

| | | | | |
|---|---|---|---|---|
| 7,211,790 B2* | 5/2007 | Ogata | ................ | G01N 30/8675 250/281 |
| 7,561,006 B2* | 7/2009 | Dutta | ...................... | H01L 23/66 333/156 |
| 8,299,873 B2* | 10/2012 | Wang | ...................... | H01P 1/184 333/161 |
| 2002/0017963 A1* | 2/2002 | Shimamoto | ............... | H01P 3/08 333/1 |
| 2002/0105395 A1* | 8/2002 | Tajima | ................ | H01P 1/20381 333/245 |
| 2004/0025566 A1 | 2/2004 | Gass et al. | | |
| 2007/0236864 A1 | 10/2007 | Goetz | | |
| 2009/0242751 A1 | 10/2009 | Gabeler | | |
| 2011/0085852 A1 | 4/2011 | Ferrara | | |

OTHER PUBLICATIONS

International Search Report and Written Opinion dated Oct. 4, 2016 from related International Application No. PCT/US2016/040086.

* cited by examiner

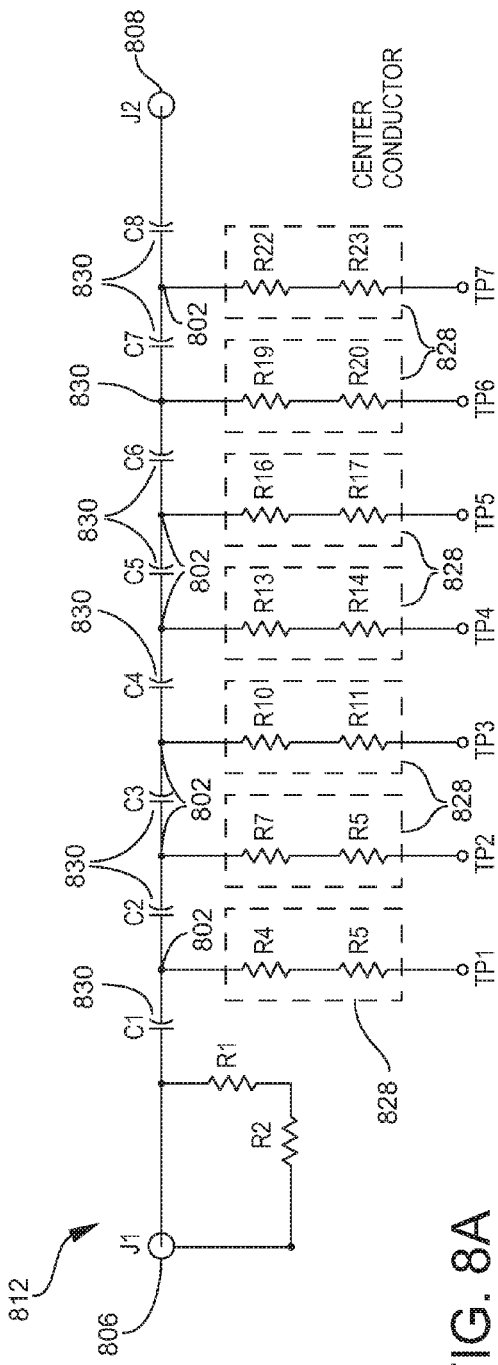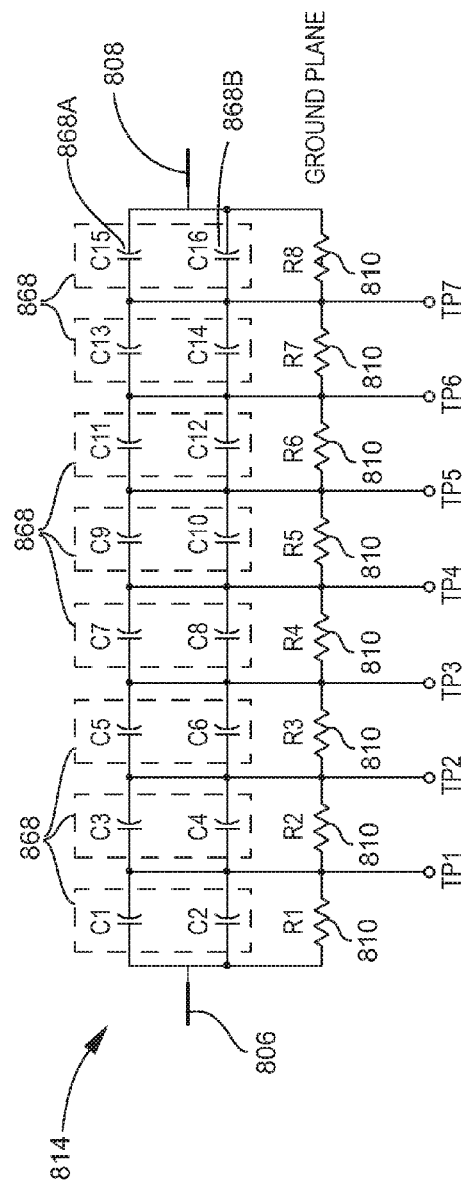
FIG. 8A
FIG. 8B

ALTERNATING CURRENT (AC) COUPLER FOR WIDEBAND AC SIGNALS AND RELATED METHODS

TECHNICAL FIELD

The present invention relates to an alternating current (AC) coupler for wideband AC signals with large DC offset voltages, such as may be employed in the processing of output signals generated by an ion detector in conjunction with spectrometry such as mass spectrometry (MS) and/or ion mobility spectrometry (IMS).

BACKGROUND

A spectrometry system in general includes an ion source for ionizing analytes of a sample of interest, an ion analyzer for separating the analyte ions based on a discriminating attribute, an ion detector for counting the separated ions, and electronics (including, for example, a data acquisition system) for processing output signals from the ion detector as needed to produce user-interpretable spectral information. The spectral information may be utilized to determine the molecular structures of components of the sample, thereby enabling the sample to be qualitatively and quantitatively characterized.

In a mass spectrometry (MS) system, the ion analyzer is a mass analyzer that separates the ions based on their differing mass-to-charge ratios (or m/z ratios, or more simply "masses"). Depending on design, the mass analyzer may separate ions by utilizing electric and/or magnetic fields, or a time-of-flight tube in the case of a time-of-flight mass spectrometer (TOFMS) that determines the m/z ratio of an analyte ion by measuring its arrival time at the ion detector. The ion detector receives the separated ions and outputs measurement signals to electronics configured for processing the signals as needed to produce a mass spectrum. The mass spectrum is typically presented as a plot containing a series of peaks indicative of the relative abundances of detected ions as a function of their m/z ratios.

In an ion mobility spectrometry (IMS) system, the ion analyzer is a drift cell that separates ions based on their different collision cross-sections. In low-field drift-time IMS techniques, ions are pulled through the drift cell by a DC voltage gradient in the presence of a drift gas. Ions of differing collision cross-sections have differing mobilities through the gas environment and hence arrive at the ion detector at different drift times. The ion detector receives the separated ions and outputs measurement signals to electronics configured for processing the signals as needed to produce a drift spectrum. The drift spectrum is typically presented as a plot containing a series of peaks indicative of the relative abundances of detected ions as a function of their drift time through the drift cell.

In some spectrometry systems referred to as ion mobility-mass spectrometry systems (IM-MS), an IM drift cell is coupled with a mass analyzer to provide unique two-dimensional information about an analyte under investigation. Additionally, in some MS, IMS, and IM-MS systems, the sample supplied to the ionization apparatus may first be subjected to a form of analytical separation such as, for example, liquid chromatography (LC) or gas chromatography (GC). In such cases, the output of the LC or GC column (chromatographically separated analytes of the sample) may be transferred into the ionization apparatus through appropriate interface hardware.

To achieve high resolution and ion measurement accuracy, as an example, the timing of narrow output pulses (e.g., 400 picoseconds (ps) to 3 nanoseconds (ns)) from the ion detector must be determined within a very narrow timing window (e.g., 100 ps). The ion detector may not offer intrinsic blocking of the high voltages associated with the operation of the ion accelerator and ion detector. The output pulses from such a detector may have a direct current (DC) offset on the order of kilovolts (kV) from ground, for example 15 kV from ground. To enable the data acquisition system that receives the output from the detector to operate at a potential that is close to ground, an alternating current (AC) coupler may be coupled between the output of the ion detector and the input of the data acquisition system. The AC coupler rejects or filters the DC component of the signal, effectively normalizing the output pulses to a zero mean or a DC offset of zero. In addition to preserving the critical timing information embodied in the detector output pulses, the AC coupler must also maintain amplitude accuracy over a potentially wide range (e.g., 5 millivolts (mV) to 5 V) for accurate quantitation.

An AC coupler known in the art consists of two 50-Ohm ($\Omega$) Subminiature version A (SMA) coaxial radio frequency (RF) connectors configured for threaded coupling to standard coaxial RF cables. The center conductors of these input and output SMA connectors are connected through a pair of coupling capacitors (also known as DC-blocking capacitors) in series, while the outer shells of the SMA connectors are connected through a similar pair of coupling capacitors in series. This known AC coupler also includes high-value resistors shunting the capacitors to equalize the DC voltage drops across the capacitors, allowing capacitors with lower voltage ratings to withstand the applied DC voltage. These resistors have no effect on the desired signals passing through the AC coupler. The known AC coupler may handle the DC common mode offset and the low-frequency components of the normal mode signal adequately. However, the known AC coupler may not transmit the high-frequency components accurately, resulting in distorted pulses, extra pulses, or ringing waveforms, depending on the specifics of the connections to the MS system. Anomalies that the data analysis software resolves as separate peaks will be erroneously identified as ions that are not actually present in the sample under analysis. Peak broadening degrades mass resolution, possibly hiding smaller nearby peaks entirely. Extended tails appended to peaks shift the effective baseline, introducing nonlinearity in sample quantitation. Typical approaches taken to compensate for ringing may also shift the assumed baseline, with similar effects.

The connectors, capacitors, interconnecting conductors, and dielectric materials that make up the AC coupler form a transmission line through which the signals pass. Each region of uniform geometry along the length of the AC coupler has a specific characteristic impedance. A signal that is incident on a transition from one geometry to another is split into a transmitted component and a reflected component. Multiple reflections can occur as a signal passes through the AC coupler, separated in time by the transmission delays between the impedance transitions. These reflections should be minimized in order to preserve the critical timing and amplitude properties needed for correct interpretation of the signal received by the data acquisition system.

Certain features of conventional AC couplers are likely to promote undesired reflections. One feature is abrupt turns in the signal path, such as a 90-degree turn in passing from the input coaxial connector to the plane of the capacitors, followed by another 90-degree turn in passing from the plane of the capacitors to the output coaxial connector. Another feature is abrupt transitions in the sizes of interconnected electrical conductors. For example, the center conductor of a coaxial connector may be 1 millimeter (mm) in diameter and directly connected to a signal trace that is 10 mm in width. Another feature is the direct connection between the unbalanced input coaxial connector and output coaxial connector to the symmetrical parallel-plate transmission line formed by the pairs of coupling capacitors without intervening balun transformers. This exposes the surrounding structures to the common mode component of the signal, which sees a different impedance than the normal mode component and propagates at a different velocity. These effects are dependent on both frequency and system layout, leading to uncontrolled signal distortion.

More generally, deficiencies in the configuration or construction of known AC couplers may lead to a number of problems. These problems include poor signal fidelity and thus reduced mass resolution and less effective quantitation, insufficient wideband impedance matching, sensitivity to nearby objects due to an unshielded balanced transmission line structure, the occurrence of spurious pulses leading to false ion identification, ringing and thus noisy baselines and poor linearity, unstable impedance, and lack of adjustability of impedance.

Therefore, there is an ongoing need for AC couplers that address problems such as those discussed above. There is also a need for AC couplers that provide improved impedance matched, high-voltage, wideband performance for transmitting AC signals while blocking DC offset voltages.

SUMMARY

To address the foregoing problems, in whole or in part, and/or other problems that may have been observed by persons skilled in the art, the present disclosure provides methods, processes, systems, apparatus, instruments, and/or devices, as described by way of example in implementations set forth below.

According to one embodiment, an AC coupler for transmitting high-frequency components of a wideband signal includes: an input end for receiving the wideband signal; an output end for transmitting an output signal; a signal conductor in electrical communication between the input end and the output end, the signal conductor comprising a conductive element and a signal conductor capacitor configured to block direct current (DC) components of the wideband signal while transmitting high-frequency alternating current (AC) components of the wideband signal; and a shielding structure defining a signal return path between the input end and the output end, the shielding structure being configured for conducting at least the AC components of the wideband signal in the signal return path, wherein: the signal conductor has a signal conductor width; the shielding structure has a width substantially greater than the signal conductor width to confine electric fields and currents in the shielding structure substantially to a region proximate to the signal conductor; and the signal conductor and the shielding structure are arranged as a transmission line.

According to another embodiment, an AC coupler for transmitting high-frequency components of a wideband signal includes: an input end for receiving the wideband signal; an output end for transmitting an output signal; a signal conductor in electrical communication between the input end and the output end, the signal conductor comprising a conductive element and a signal conductor capacitor configured to block direct current (DC) components of the wideband signal while transmitting high-frequency alternating current (AC) components of the wideband signal; and a shielding structure defining a signal return path between the input end and the output end, the shielding structure being configured for conducting at least the AC components of the wideband signal in the signal return path, wherein: the signal conductor has a signal conductor width; the shielding structure has a width substantially greater than the signal conductor width; the shielding structure is spaced from the signal conductor by an offset distance orthogonal to the width of the shielding structure; the difference between the width of the shielding structure and the signal conductor width is substantially greater than the offset distance; and the signal conductor and the shielding structure are arranged as a transmission line.

According to another embodiment, a spectrometer includes: an AC coupler according to any of the embodiments disclosed herein; and an ion detector communicating with the input end.

According to another embodiment, a method for making an AC coupler includes: arranging a signal conductor and a shielding structure as a transmission line configured for transmitting high-frequency components of a wideband signal from an input connector to an output connector, wherein: the signal conductor is configured for being interconnected between respective center conductors of the input connector and the output connector, and the signal conductor comprises a conductive element and a capacitor configured to block direct current (DC) components of the wideband signal while transmitting high-frequency alternating current (AC) components of the wideband signal; and the shielding structure is configured for being interconnected between respective shielding conductors of the input connector and the output connector, and for conducting at least the AC components of the wideband signal, and the shielding structure has a width substantially greater than a width of the signal conductor to confine electric fields and currents in the shielding structure substantially to a region proximate to the signal conductor.

According to another embodiment, a method for making an AC coupler includes: arranging a signal conductor and a shielding structure as a transmission line configured for transmitting high-frequency components of a wideband signal from an input connector to an output connector, wherein: the signal conductor is configured for being interconnected between respective center conductors of the input connector and the output connector, and the signal conductor comprises a conductive element and a capacitor configured to block direct current (DC) components of the wideband signal while transmitting high-frequency alternating current (AC) components of the wideband signal; the shielding structure is configured for being interconnected between respective shielding conductors of the input connector and the output connector, and for conducting at least the AC components of the wideband signal; the shielding structure has a width substantially greater than a width of the signal conductor; the shielding structure is spaced from the signal conductor by an offset distance orthogonal to the width of the shielding structure; and the difference between the width of the shielding structure and the width of the signal conductor is substantially greater than the offset distance.

Other devices, apparatus, systems, methods, features and advantages of the invention will be or will become apparent to one with skill in the art upon examination of the following figures and detailed description. It is intended that all such additional systems, methods, features and advantages be included within this description, be within the scope of the invention, and be protected by the accompanying claims.

BRIEF DESCRIPTION OF THE DRAWINGS

The invention can be better understood by referring to the following figures. The components in the figures are not necessarily to scale, emphasis instead being placed upon illustrating the principles of the invention. In the figures, like reference numerals designate corresponding parts throughout the different views.

FIG. 8A is a circuit diagram of an example of a central signal conductor according to some embodiments.

FIG. 8B is a circuit diagram of an example of a shielding structure according to some embodiments.

DETAILED DESCRIPTION

Figure 1:
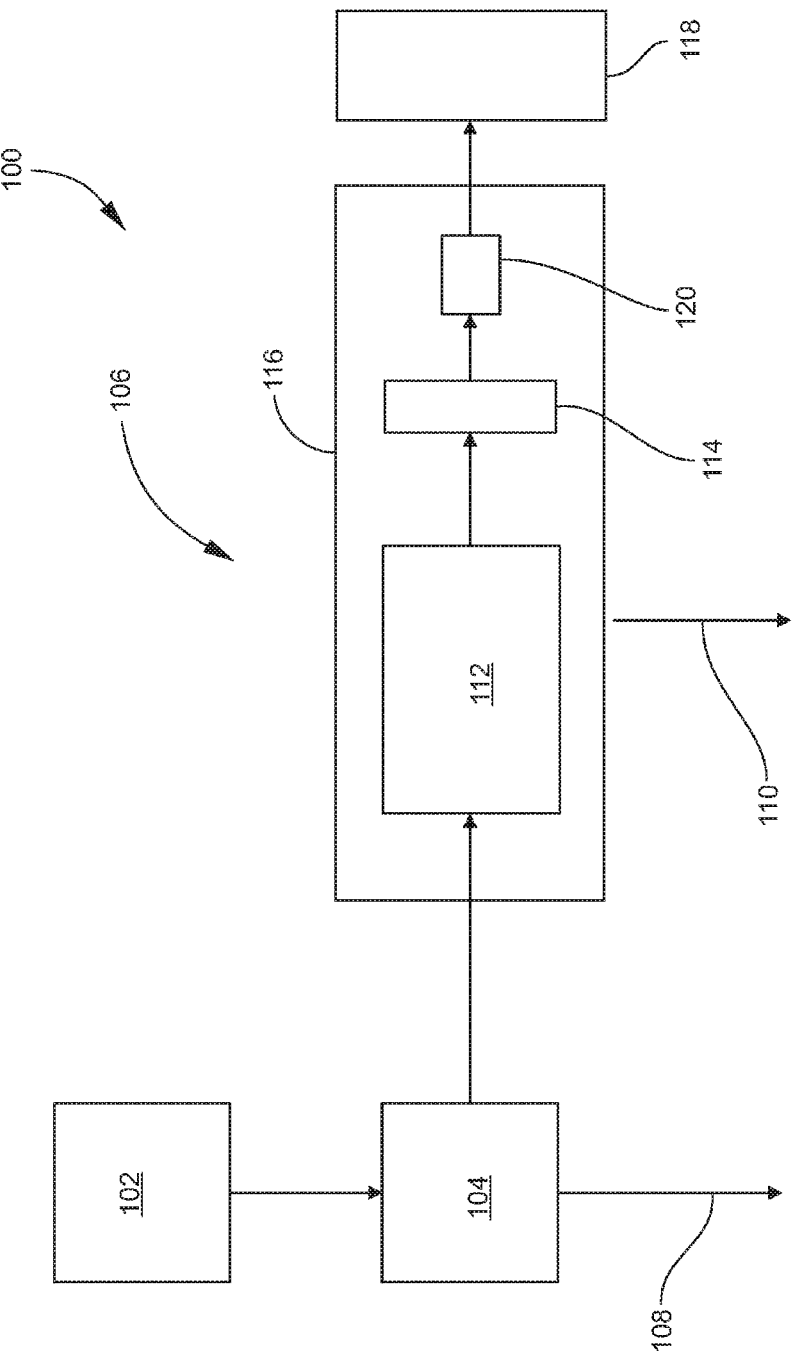
FIG. 1 is a schematic view of an example of a spectrometry system according to some embodiments.

FIG. 1 is a schematic view of an example of a spectrometry system 100 according to some embodiments. The spectrometry system 100 generally includes a sample source 102, an ion source 104, and a spectrometer 106. The spectrometer 106 may generally include an ion analyzer 112 and an ion detector 114 enclosed in a housing 116. The spectrometry system 100 may be a mass spectrometry (MS) system, ion mobility spectrometry (IMS) system, or hybrid ion mobility-mass spectrometry (IM-MS) system, as described generally above. Hence, the ion analyzer 112 schematically depicted in FIG. 1 may be a mass analyzer (or more than one mass analyzer in tandem configurations), an IM drift cell, or an IM drift cell followed by a mass analyzer.

In some embodiments, the subject matter disclosed herein is particularly advantageous when implemented with pulsed-beam analyzers such as, for example time-of-flight (TOF) analyzers. In time-of-flight mass spectrometry (TOFMS), the m/z ratio of an ion is determined by measuring the time of arrival of the ion at the ion detector 114 after the ion has traveled through a known path length under known conditions. TOFMS utilizes a high-resolution mass analyzer (TOF analyzer) in the form of an electric field-free flight tube. An ion beam is transmitted into an ion accelerator (or pulser), which applies a pulsed electric field of known strength to accelerate ions from the ion beam in pulses (or ion "packets") into the flight tube. This acceleration ideally results in an ion having the same kinetic energy as every other ion. The velocity of the ion depends on the mass-to-charge ratio. The time that it subsequently takes for the ion to reach the ion detector 114 at a known distance is measured. This time will depend on the mass-to-charge ratio of the ion (e.g., heavier ions travel at lower velocities in comparison to lighter ions). From this time and the known experimental parameters one can find the mass-to-charge ratio of the ion. Another example of a pulsed-beam analyzer is an ion mobility drift cell, described above.

Generally, the ion detector 114 may be any device configured for collecting and measuring the flux (or current) of analytically separated ions (separated by m/z ratio and/or collision cross-section) outputted from the ion analyzer 112. In some embodiments, the subject matter disclosed herein is particularly advantageous when implemented with an electron multiplier (EM) or a micro-channel plate (MCP) detector.

The ion detector 114 may be coupled to a data acquisition system 118 configured for receiving output pulses from the ion detector 114. The output pulses may be representative of the abundance of ions arriving at the ion detector 114 after the ions have been separated by the mass analyzer 112 according to m/z ratio (either directly or as derived from times-of-flight). The output pulses from the ion detector 114 may have an AC component (e.g., the pulses representative of the separated ions) and a DC component (e.g., a DC offset to the output pulses). As an example, the AC component of the output pulse signal may have a signal amplitude range of 5 mV to 5 V and the DC component may have a magnitude that is several orders greater (e.g., 15 kV). However, the data acquisition system 118 may need to operate with a DC component or mean signal potential level of near to or substantially equal to zero (0) V or ground. In embodiments disclosed herein, this is addressed by providing an AC coupler 120 in the signal path between the ion detector 114 and the data acquisition system 118. As described by examples of embodiments below, the AC coupler 120 is configured to receive the output pulses from the ion detector 114 and normalize the output pulses by removing all or substantially all of the DC component (and low-frequency components below some cut-off frequency) from the output pulses. In this manner, the output signals from the AC coupler 120 are substantially equal to the AC components of the output pulses from the ion detector 114. Depending on the embodiment, the AC coupler 120 may be considered as being a part of or integrated with the ion detector 114, or as a device separate and distinct from the ion detector 114.

Figure 2:
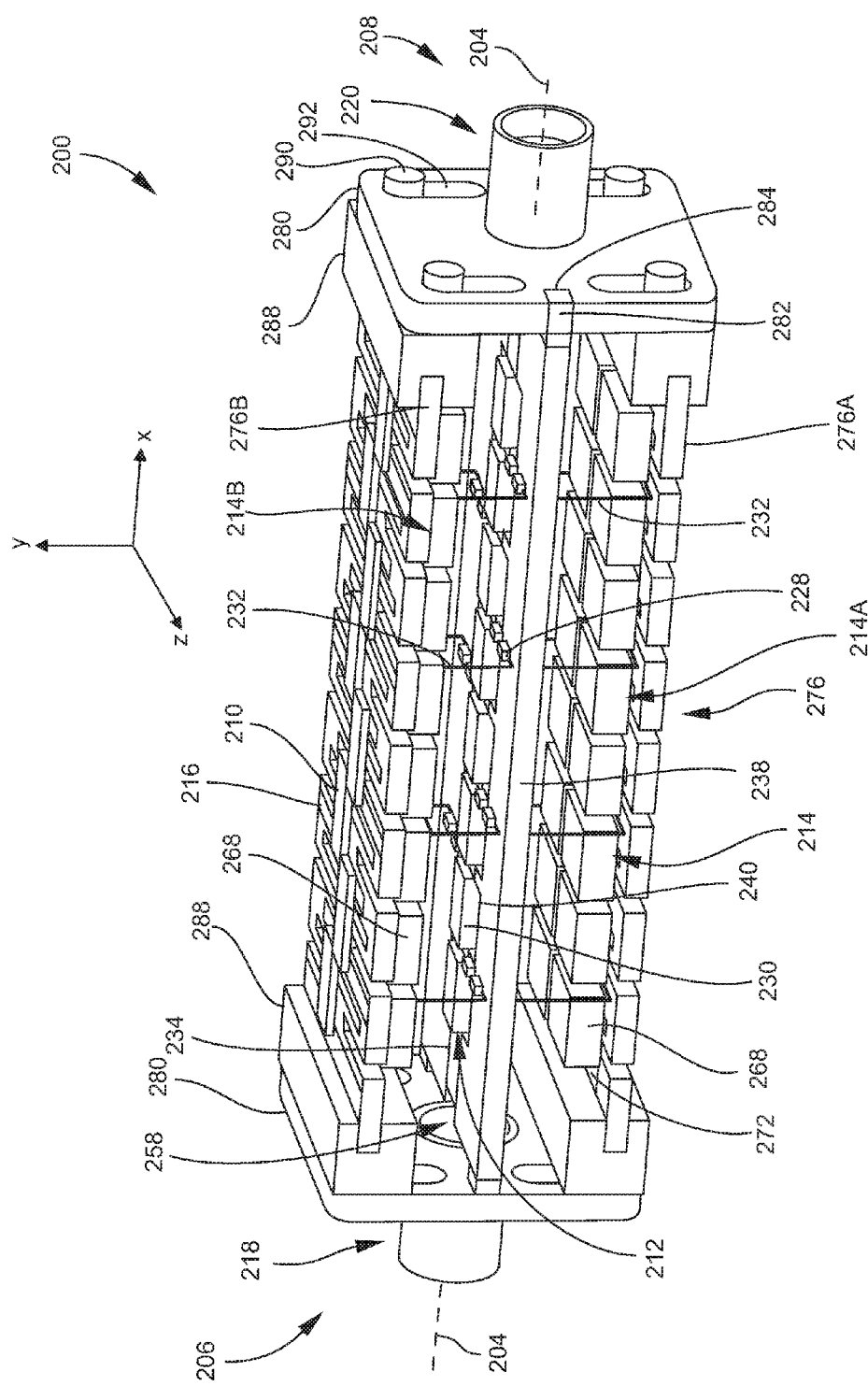
FIG. 2 is a perspective view of an example of an AC coupler according to some embodiments.

FIG. 2 is a perspective view of an example of an AC coupler 200 according to some embodiments. The AC coupler 200 is generally positioned along a longitudinal axis 204 between an input end (node) 206 and an output end (node) 208. For illustrative purposes, FIG. 2 includes a Cartesian x-y-z coordinate frame of reference, with the longitudinal axis 204 corresponding to the x-axis. Lengths, thicknesses, and widths of components are considered along the x-axis, y-axis, and z-axis, respectively. The x-axis, y-axis, and z-axis may also be referred to as the x-direction, y-direction, and z-direction, respectively.

Generally, the AC coupler 200 is configured for impedance-matched transmission of wideband (particularly high-frequency) AC signals from the input end 206 to the output end 208, while blocking (or substantially blocking) DC offset voltages, such that the DC offsets are not transmitted to the output end 208. For example, the AC coupler 200 may receive output pulses from an ion detector 114 (FIG. 1) at the input end 206. Each output pulse is composed of an AC component and a DC component (DC offset). The AC coupler 200 transmits the AC component of the output pulses to the output end 208 but rejects the DC components of the output pulses. Consequently, the AC coupler 200 isolates the circuitry (signal processing or data acquisition electronics 118, FIG. 1) communicating with the output end 208 from the DC component, which may constitute a significantly high-voltage offset relative to ground (e.g., on the order of kV as noted above). The AC coupler 200 is configured to transmit high-frequency signals with high fidelity, including at the high frequencies encountered when processing ion detector signals and particularly TOF detector signals (e.g., on the order of GHz, such as 3 GHz and higher). In the present context, the term "DC" is understood to encompass zero frequency and also a range of low frequencies, unless specified otherwise or the context dictates otherwise. Thus, for example, "DC" may correspond to a range from 0 to 6 kHz.

For these purposes, the AC coupler 200 may generally be configured as a non-resonant, self-shielding transmission line with DC blocking functionality. For example, in the illustrated embodiment the AC coupler 200 generally includes a central (inner) signal conductor 212 and an outer shielding structure (or shielding conductor) 214 spatially separated from the signal conductor 212. The intervening space between the signal conductor 212 and the shielding structure 214 may be an open gap (air or vacuum), a solid dielectric material, or a combination of both. The signal conductor 212 generally extends along the longitudinal axis 204, and the shielding structure 214 is spaced from the signal conductor 212 at a position offset from the longitudinal axis 204, i.e., at a radial (orthogonal) distance from the signal conductor 212 relative to the longitudinal axis 204 (or at one or more radial distances, given that the shielding structure 214 may have surfaces or features at different elevations relative to each other). The signal conductor 212 and the shielding structure 214 may form an unbalanced transmission line in which the respective impedances of the signal conductor 212 and the shielding structure 214 are unequal relative to ground. The signal conductor 212, or both the signal conductor 212 and the shielding structure 214, include one or more coupling capacitors effective for blocking DC and low-frequency components of the signal. Generally, the shielding structure 214 is configured to provide a low impedance path from a signal return connection at the input end 206 to a ground connection at the output end 208 for at least the AC components of the currents seen in the shielding structure 214. In some embodiments, the shielding structure 214 may not block DC components, i.e., the shielding structure 214 is low impedance down to DC, and the AC coupler 200 blocks only normal mode DC voltages. In other embodiments, particularly those involving common mode voltages of several kilovolts, the shielding structure 214 may function to block DC components, in which case the shielding structure 214 also includes one or more coupling capacitors, and the AC coupler 200 blocks both normal mode and common mode DC voltages.

In some embodiments, the AC coupler 200 may have a generally planar geometry (e.g., similar to a stripline or microstrip transmission line), as in the illustrated embodiment. In this case the signal conductor 212 and the shielding structure 214 are generally planar structures and are generally spatially (physically) parallel to each other. The shielding structure 214 may be a single planar structure positioned at an offset distance from the signal conductor 212, or may include two planar structures positioned at respective offset distances from the signal conductor 212 on opposite sides of the signal conductor 212. That is, the shielding structure 214 may include a first shielding structure 214A and a second shielding structure 214B as in the illustrated embodiment.

Alternatively, the AC coupler 200 may have a generally coaxial geometry (e.g., similar to a coaxial transmission line), in which case the signal conductor 212 and the shielding structure 214 are generally cylindrical or prismatic structures and the shielding structure 214 coaxially surrounds the signal conductor 212. In the coaxial case the shielding structure 214 may include a single cylindrical or prismatic structure or a plurality of such structures spaced from each other (circumferentially or along a polygonal perimeter) about the longitudinal axis 204 and collectively surrounding the signal conductor 212 at the radial offset distance(s). Thus, in the present context the term "coaxial" refers to a shielding structure surrounding a central signal conductor at some radial offset distance from the central longitudinal axis of the central signal conductor, and encompasses shielding structures having prismatic geometries as well as shielding structures having cylindrical geometries. One example of an AC coupler with coaxial prismatic geometry is described further below in conjunction with FIGS. 15 to 18. Moreover, in other embodiments more than one signal conductor may be provided, as described below in conjunction with examples illustrated in FIGS. 11 to 14.

Figure 3:
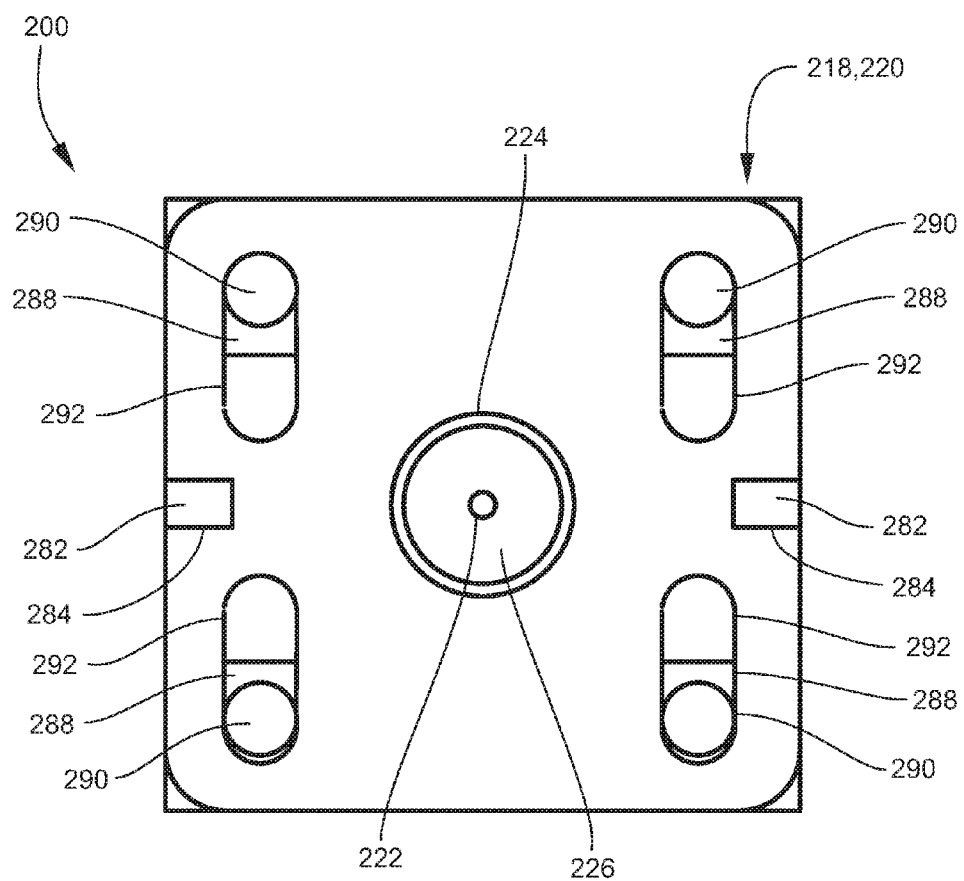
FIG. 3 is an end view of the AC coupler illustrated in FIG. 2.

As also shown in FIG. 2, an AC input connector 218 and an AC output connector 220 may be provided at the input end 206 and the output end 208, respectively. Reference is also made to FIG. 3, which is an end view of the AC coupler 200 representative of either the input connector 218 or the output connector 220. In a typical embodiment, the input and output connectors 218 and 220 have a standard configuration for connecting to standard AC transmission lines. For example, the input and output connectors 218 and 220 may be 50-Ohm RF coaxial connectors of standard configuration for connecting to 50-Ohm RF coaxial cables. Thus, as illustrated, the input and output connectors 218 and 220 each may include a center conductor 222 coaxially surrounded by an outer shield 224, and an annular dielectric 226 between the center conductor 222 and the outer shield 224. The center conductors 222 of the input and output connectors 218 and 220 electrically communicate with the signal conductor 212 of the AC coupler 200, and the outer shields 224 electrically communicate with the shielding structure 214. The input and output connectors 218 and 220 may be sized the same as each other or differently from each other. In some embodiments and as illustrated, the input connector 218 and the output connector 220 are oriented such that they are positioned on the longitudinal axis 204 in common with the signal conductor 212. Consequently, the signal path from the input connector to the AC coupler 200 and from the AC coupler 200 to the output connector is collinearly aligned, avoiding abrupt physical turns, which may reduce signal reflections.

Generally, an AC coupler may be constructed as a transmission line capable of passing signals in a high-frequency (e.g., GHz) range by adding one or more capacitors in series with the electrically conductive lines (e.g., strips, traces, etc.) of the signal conductor to block the DC and low-frequency components of the signals. As long as the capacitors are small in comparison with the cross-sectional dimensions of the transmission line structure, the high-frequency performance of the line may be maintained. When the series capacitors are required to block a high DC potential offset on the order of kV (e.g., 10 kV or more), in conventional solutions the minimum size of the capacitors becomes much larger than the dimensions of typically small transmission lines, leading to impedance variations that cause reflections and signal distortion. However, embodiments of the AC coupler 200 disclosed herein combine the broadband performance of a transmission line with the DC blocking ability of large series capacitors by providing an arrangement of one or more capacitors and conductive interconnections that reduces the need to employ undesirably large capacitors and maintains good transmission line performance where large capacitors must be used. In some embodiments, the capacitor(s) utilized in the AC coupler 200 are leadless multilayer capacitors. In some embodiments, the arrangement entails replacing the bulk of the conductors with capacitors along the length of the AC coupler 200. In optimal embodiments, the arrangement is such that the distributions of electrical currents and electromagnetic fields in the AC coupler 200 closely approximate the corresponding distributions in the ideal transmission line, thus ensuring comparable high-frequency performance.

Moreover, according to embodiments disclosed herein the width (along the z-axis) of the shielding structure 214 may be substantially greater than the width of the signal conductor 212, thereby providing effective shielding for the signal conductor 212, minimizing sensitivity to surrounding objects, and eliminating (or substantially eliminating) problems with common mode signal propagation. In further embodiments, these advantages are enhanced by the width of the shielding structure 214 being substantially greater than the spacing (along the y-axis), or "offset distance," between the signal conductor 212 and the shielding structure 214. Examples of realizing such configurations are described below.

In some embodiments, the planar geometry described above and further below may be preferred over a coaxial geometry due to relatively simpler and lower-cost construction. Moreover, the planar geometry facilitates configuring the AC coupler 200 to be adjustable or tunable for the purpose of impedance matching, as described further below. Impedance adjustability is desirable for attaining very low reflection coefficients. In some embodiments, the AC coupler 200 has a reflection coefficient of less than 20%. In some embodiments, the AC coupler 200 has a voltage standing wave ratio (VSWR) of less than 1.5:1. In some embodiments, it is desirable that the AC coupler 200 not introduce anomalies larger than the 1% to 2% level set by other parts of the system. However, while the planar geometry may be preferred over a coaxial geometry generally, the present disclosure provides an example of an AC coupler with coaxial prismatic geometry, described further below in conjunction with FIGS. 15 to 18. The coaxial prismatic geometry described below may provide one or more of the same advantages as the planar geometry, as the coaxial prismatic geometry is based on planar structures and may be configured for adjusting impedance.

Figure 4A:
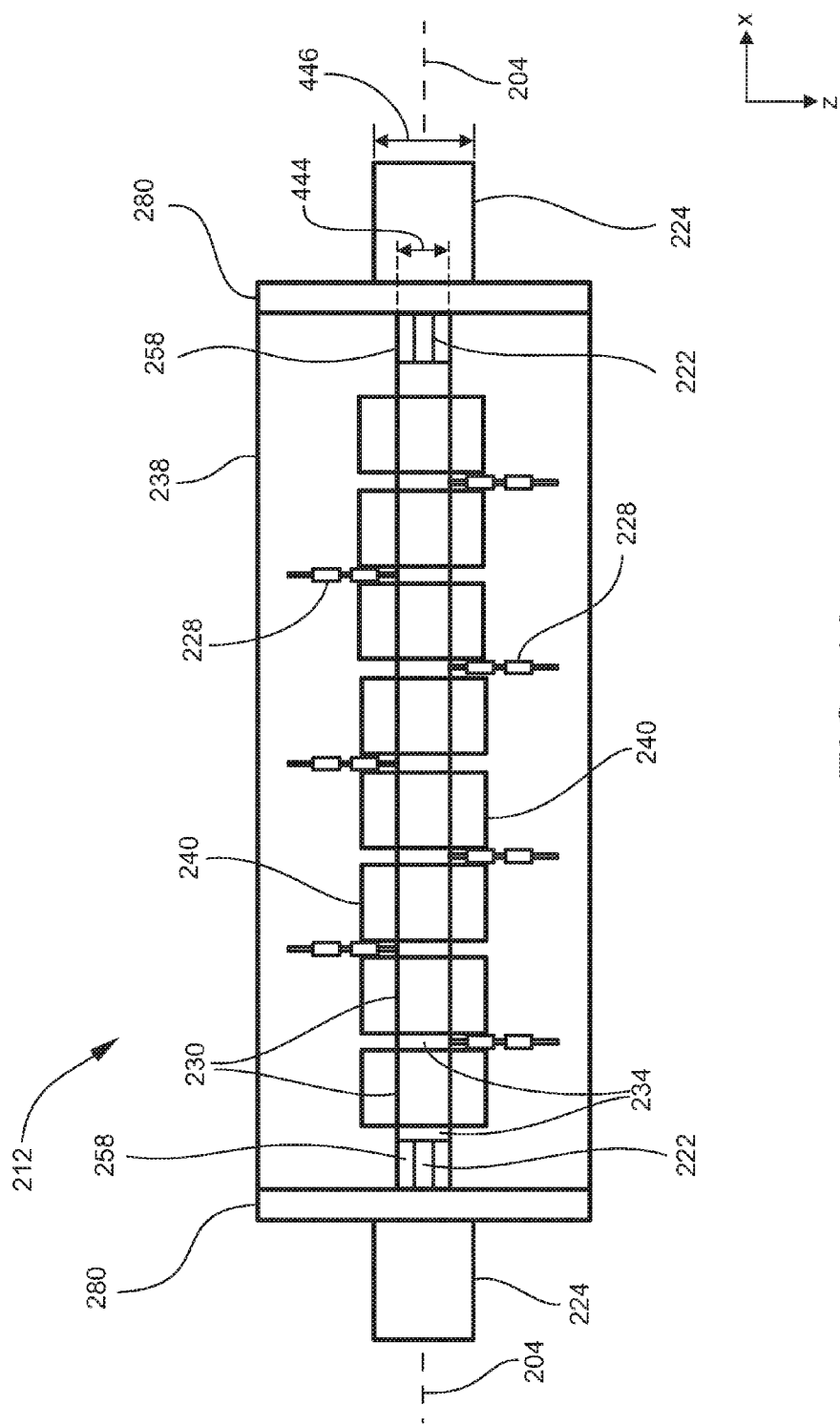
FIG. 4A is a top plan view of a central signal conductor that may be provided in an AC coupler according to some embodiments.
Figure 4B:
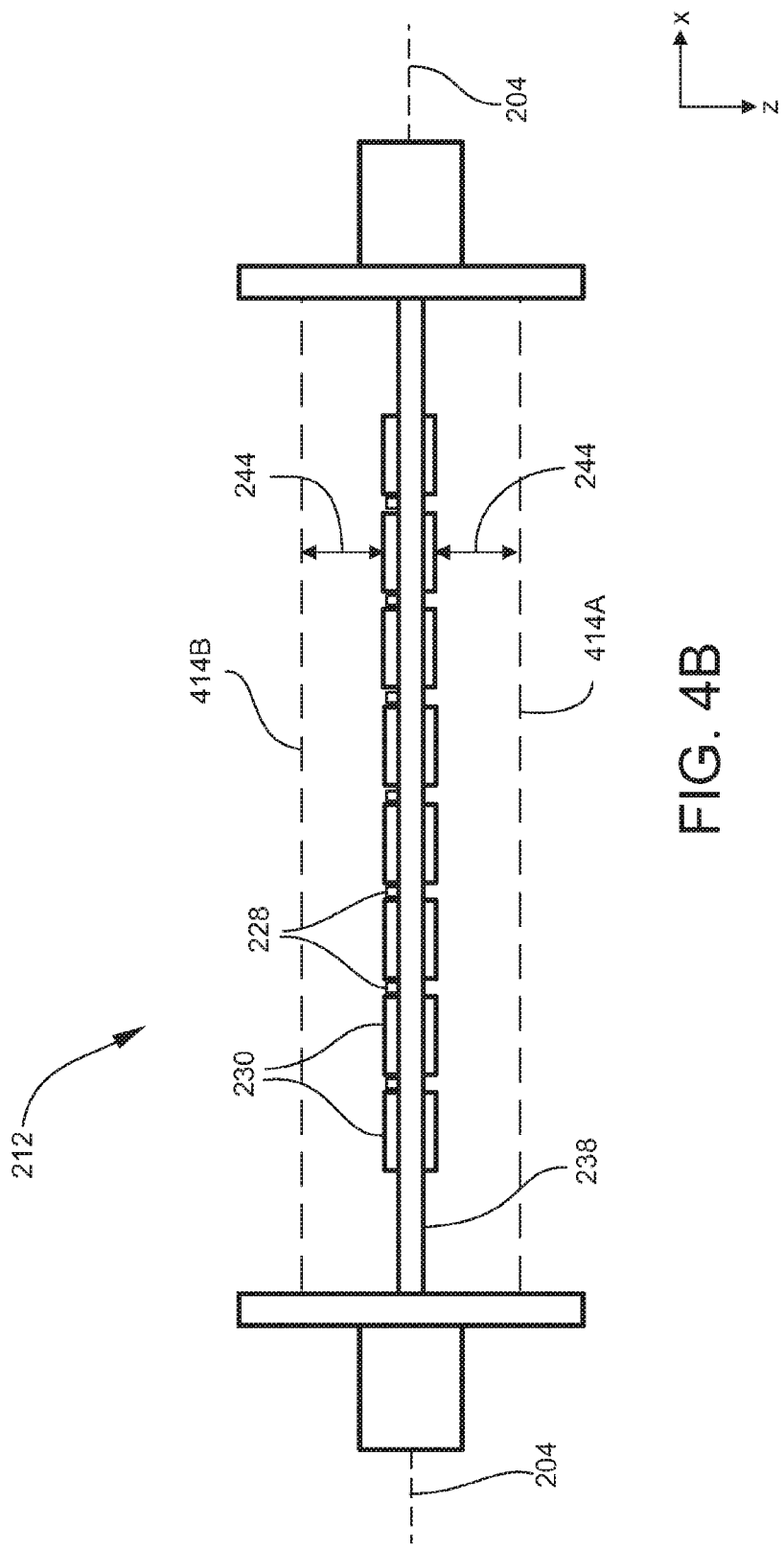
FIG. 4B is a side view of the signal conductor illustrated in FIG. 4A.

FIG. 4A is a top plan view of the signal conductor 212, and FIG. 4B is a side view of the signal conductor 212. In the embodiment illustrated in FIGS. 2, 4A and 4B, the signal conductor 212 includes a plurality of signal conductor capacitors 230 and a plurality of conductive elements 234 (e.g., strips, traces, etc.) interconnecting adjacent signal conductor capacitors 230, with one of the conductive elements 234 coupled to the center conductor 222 of the input connector 218 (at the input end 206) and another coupled to the center conductor 222 of the output connector 220 (at the output end 208). The signal conductor capacitors 230 and the conductive elements 234 are arranged or centered on the longitudinal axis 204 between the input end 206 and the output end 208. In the illustrated embodiment the signal conductor capacitors 230 are connected in series. In other embodiments, one or more of the signal conductor capacitors 230 may be connected in parallel. The signal conductor capacitors 230 and the conductive elements 234 may be supported on a planar central (or inner) dielectric substrate 238 composed of a suitable dielectric material such as, for example, a printed circuit laminate, organic polymer, ceramic, etc. The central dielectric substrate 238 may be of a size determinative of the overall geometry of the AC coupler 200. The conductive elements 234 may be composed of copper, silver, gold, or other suitable conductive material. The conductive elements 234 may be deposited or laminated as a pattern on the central dielectric substrate 238, or may be separate elements such as metal foils disposed on the central dielectric substrate 238.

In some embodiments, the central dielectric substrate 238 may include openings 240 (e.g., recesses, pockets, through-holes, slots, cut-outs, etc.) in which the signal conductor capacitors 230 are positioned. By this configuration, the signal conductor capacitors 230 are coplanar or substantially coplanar with the central dielectric substrate 238, thereby minimizing variations in the effective thickness (y-axis) of the signal conductor 212. Moreover, the thickness of the signal conductor capacitors 230 may be the same or substantially the same as the thickness of the central dielectric substrate 238 such that, after being mounted in the openings 240, the signal conductor capacitors 230 are flush with the outer surface of the central dielectric substrate 238 or protrude only a small distance above the outer surface, as shown for example in FIG. 4B. As best shown in FIG. 4A, the width (z-axis) of the signal conductor capacitors 230 may be the same or substantially the same as the width of the conductive elements 234 interconnecting them. Matching the thickness of the signal conductor capacitors 230 with the thickness of the central dielectric substrate 238, and/or matching the width of the signal conductor capacitors 230 with the width of the conductive elements 234, maintains a more uniform effective geometry for the electric fields and current along the length of the signal conductor 212, thereby minimizing fluctuations in the characteristic impedance of the transmission line structure of the AC coupler 200.

In an embodiment including openings 240, conductive elements 234 may be located on both sides of the central dielectric substrate 238, with the ends of each signal conductor capacitors 230 being electrically connected to both top and bottom conductive elements 234. In this case, the vertical surfaces of the openings 240 between the capacitors 230 may be metallized, connecting the top and bottom conductive elements 234. The ends of the capacitors 230 may likewise be metallized, with the metal extended onto the top and bottom faces of the capacitors 230 for a short distance. The spaces between the ends of the capacitors 230 and the vertical faces of the dielectric substrate 238 may be filled with solder to form the electrical and mechanical connections.

It is seen that coupling the AC coupler 200 at its input end 206 to an input connector 218 and at its output end 208 to an output connector 220 results in a series of three transmission lines having different geometries. In the illustrated embodiment, the AC coupler 200 has a planar geometry and is coupled between coaxial connectors 218 and 220 at the input end 206 and the output end 208, respectively, to facilitate connections to standard coaxial cables. Even when the AC coupler 200 alternatively has a coaxial geometry, the AC coupler 200 still does not have the same exact geometry as that of the input and output coaxial connectors 218 and 220. When two transmission lines having different geometries are joined, reflections will normally be produced at the junction, even if both lines have identical characteristic impedances. These reflections may be reduced when the cross-sectional dimensions of the transmission lines are similar. Thus, in some embodiments the widths of the signal conductor capacitors 230 and conductive elements 234 are restricted to values less than inner diameters of the outer shields 224 of the input and output connectors 218 and 220, or to values between the inner diameters of the outer shields 224 and the outer diameters of the inner conductors 222 (FIG. 3) of the input and output connectors 218 and 220. This range of dimensions may also minimize the required length of any intermediate structures that may be placed in the transition regions between the AC coupler 200 and the input and output connectors 218 and 220 to further reduce reflections. In FIG. 4A, the width of the signal conductor capacitors 230 (which is the same as the width of the conductive elements 234 in the present embodiment) is indicated at 444 and the inner diameter of the outer shield 224 of the input connector 218 or output connector 220 is indicated at 446.

Because the propagation velocity of the electromagnetic waves decreases in inverse proportion to the square root of the permittivity of dielectric media, the fringing electric fields that penetrate the supporting dielectric substrate propagate more slowly than the main part of the field that is in air or vacuum. The degradation of the pulses caused by this effect may be minimized by making the openings 240 of the central dielectric substrate 238 substantially wider (z-axis) than the signal conductor capacitors 230 mounted in the openings 240. For example, in the embodiment illustrated in FIG. 2 each signal conductor capacitor 230 is centered in a corresponding opening 240 that may be substantially wider than the signal conductor capacitor 230. This configuration results in the signal conductor capacitor 230 being spaced by a lateral distance or gap from the edge of the central dielectric substrate 238 defining the opening 240. With the signal conductor capacitor 230 being centered in the wider opening 240, a gap along the z-axis exists between each lateral side of the signal conductor capacitor 230 and the lateral edge of the central dielectric substrate 238 defining the opening 240. As one non-limiting example, the overall width of the opening 240 (from one lateral edge to the other) may be in a range from 150% to 500% of the width of the signal conductor capacitor 230 or more. As another example, the overall width of the opening 240 (from one lateral edge to the other) may be about 260% of the width of the signal conductor capacitor 230. The degradation of the pulses caused by this effect may also be reduced by utilizing thinner capacitors and dielectric materials.

Figure 5A:
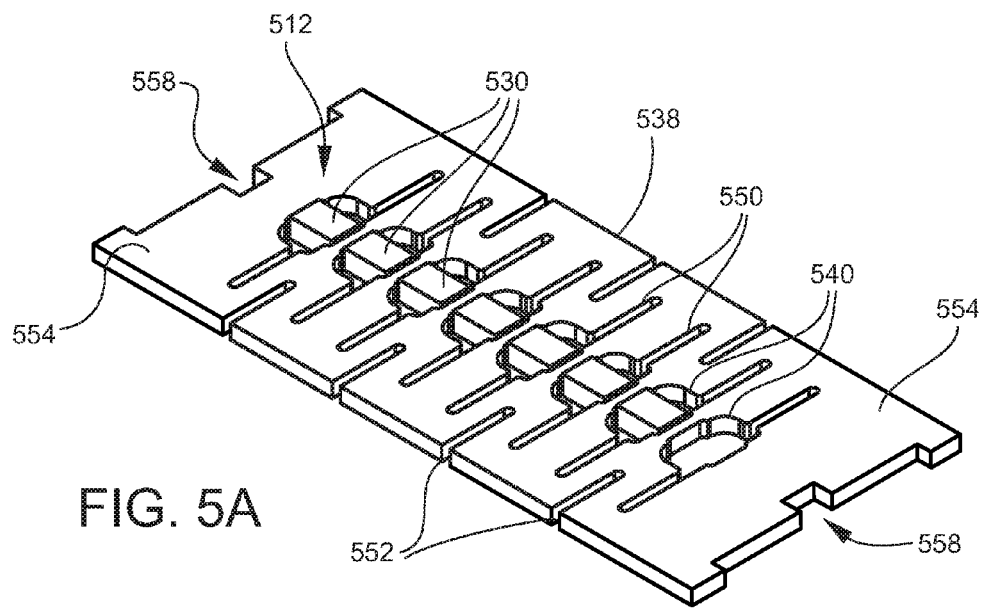
FIG. 5A is a perspective view of an example of a central signal conductor and associated central dielectric substrate according to another embodiment.
Figure 5B:
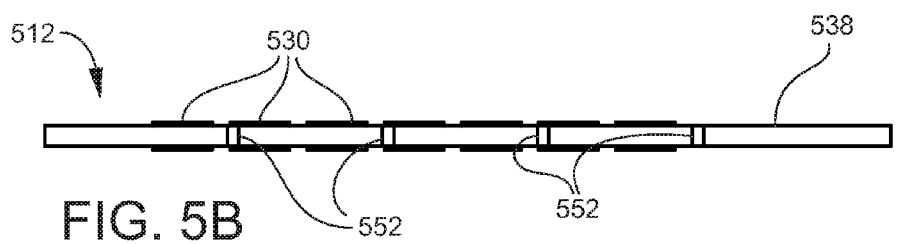
FIG. 5B is a side view of the central signal conductor and dielectric substrate illustrated in FIG. 5A.

FIG. 5A is a perspective view of an example of a central signal conductor 512 and associated central dielectric substrate 538 according to another embodiment. FIG. 5B is a side view of the central signal conductor 512 and dielectric substrate 538. The signal conductor 512 includes a plurality of series-connected signal conductor capacitors 530. The signal conductor capacitors 530 are disposed in respective openings 540 formed in the dielectric substrate 538, and are interconnected by conductive elements as described above. For illustrative purposes, the conductive elements and one of the signal conductor capacitors are not shown. FIG. 5A illustrates an alternative shape of the openings 540 that includes rounded features. FIG. 5A also illustrates an embodiment in which the dielectric substrate 538 includes a pattern of slots and transitional features such as axial end gaps, described below.

Similar to FIG. 4B, FIG. 5B shows that mounting the signal conductor capacitors 530 in openings 540 results in the signal conductor capacitors 530 being coplanar with the dielectric substrate 538, which in turn results in the assembly have a low-profile geometry that minimizes impedance discontinuities and consequently signal reflections. The low-profile geometry is further enhanced by the signal conductor capacitors 530 having about the same thickness as the dielectric substrate 538, as described above.

Figure 6:
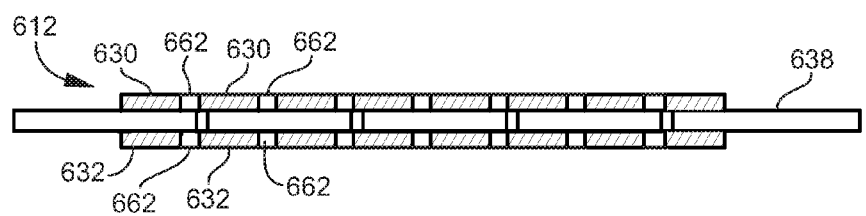
FIG. 6 is a side view of an example of a central signal conductor and associated central dielectric substrate according to another embodiment.

FIG. 6 is a side view of an example of a central signal conductor 612 and associated central dielectric substrate 638 according to another embodiment. The central signal conductor 612 includes an array of first signal conductor capacitors 630 positioned on a first side of the central dielectric substrate 638 and spaced from each other by respective intervening regions, and an array of second signal conductor capacitors 632 positioned on an opposing second side of the central dielectric substrate 638 and spaced from each other by respective intervening regions. The arrays are aligned with each other on the two opposing sides of the central dielectric substrate 638, such that the central signal conductor 612 includes a series of opposing pairs of signal conductor capacitors 630 and 632 spaced along the length of the central signal conductor 612. This configuration, however, results in the signal conductor 612 having a non-uniform thickness (along the y-axis), i.e., the thickness alternates between the combined thickness of the central dielectric substrate 638 and two opposing capacitors 630 and 632 and the thickness of the bare central dielectric substrate 638 between opposing pairs of capacitors 630 and 632. The variation in impedance caused by this non-uniform geometry may be reduced by minimizing the length (x-axis) of the intervening regions between the series-connected capacitors, such as by providing more capacitors and shorter-length conductive elements along the length of the signal conductor 612. In some embodiments, each intervening region may be occupied by a filler structure 662 of the same or similar height (i.e., the height of the filler structures 662 from the surface of the central dielectric substrate 638, along the y-axis) and width (z-axis) as the signal conductor capacitors 630 and 632, thereby reducing the geometric non-uniformities caused by the alternation between the signal conductor capacitors 630 and 632 and the conductive elements. The filler structures 662 may be conductive and/or dielectric materials.

Figure 7A:
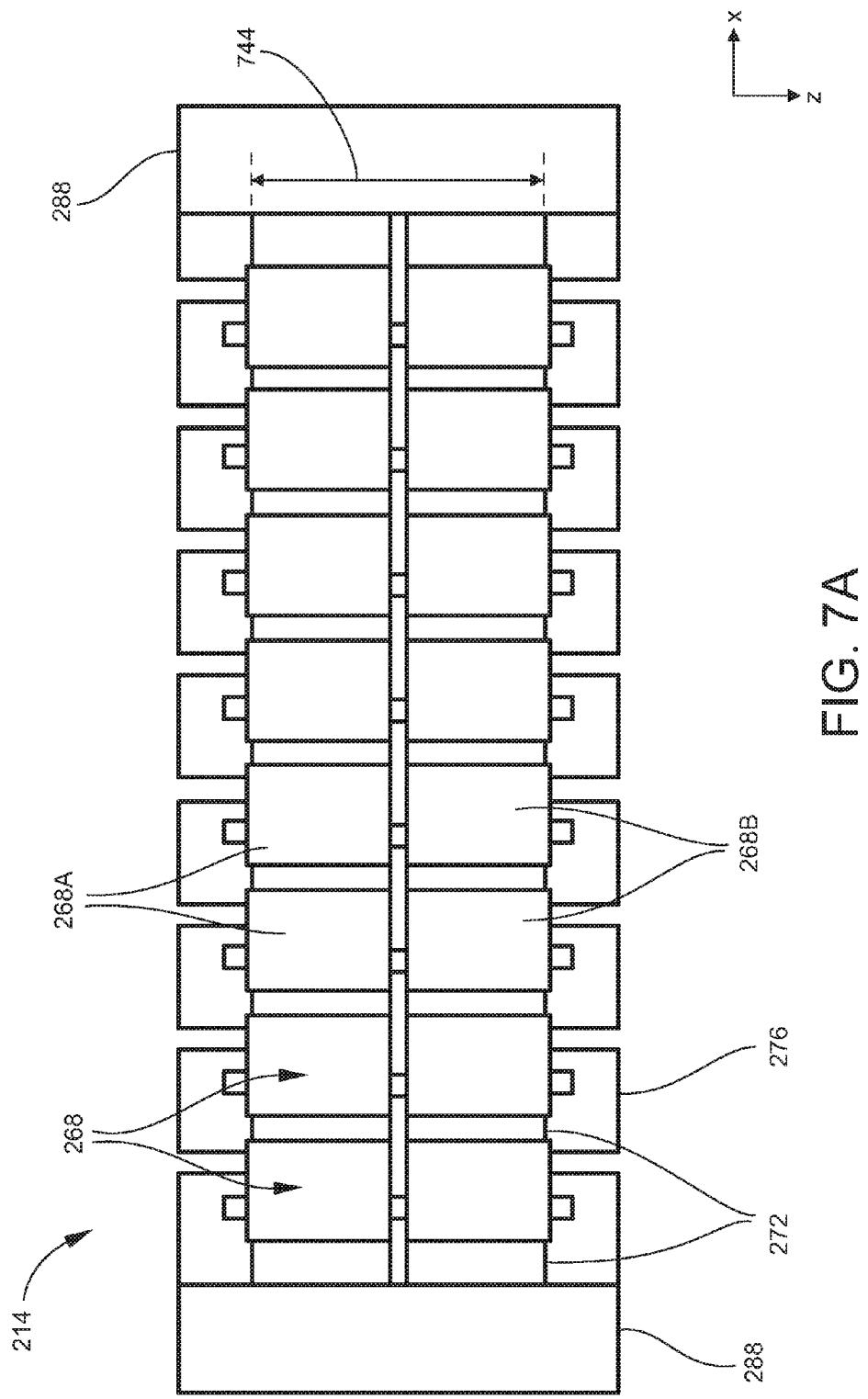
FIG. 7A is a plan view of the inner side of an outer shielding structure that may be provided in an AC coupler according to some embodiments.
Figure 7B:
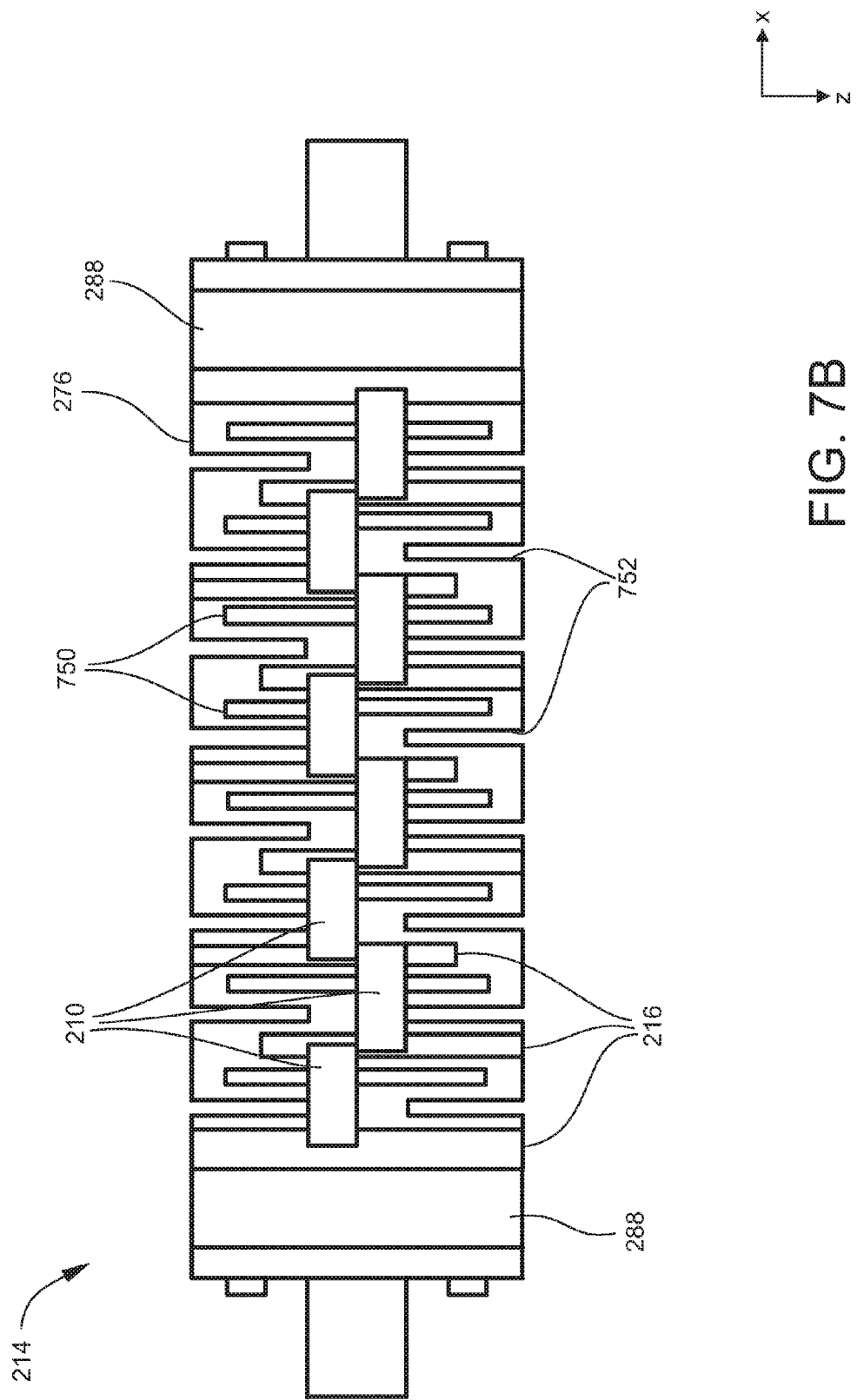
FIG. 7B is a plan view of the opposing outer side of the shielding structure illustrated in FIG. 7A.

FIG. 7A is a plan view of the inner side of the shielding structure 214 (e.g., the first shielding structure 214A or the second shielding structure 214B shown in FIG. 2), the inner side being the side facing toward the signal conductor 212 in the arrangement shown in FIG. 2. FIG. 7B is a plan view of the opposing outer side of the shielding structure 214. Generally, the shielding structure 214 is configured to provide a return current path and serve as a ground plane of the AC coupler 200. In some embodiments, the shielding structure 214 may generally be configured the same as or similar to the signal conductor 212. Thus, each shielding structure 214 may include between the input end 206 and the output end 208 (FIG. 2) one or more shielding structure capacitors 268 effective for blocking DC and low-frequency signal components, and a plurality of conductive elements 272 (e.g., strips, traces, etc.) interconnecting adjacent shielding structure capacitors 268, with one of the conductive elements 272 communicating with the outer shield 224 of the input connector 218 (at the input end 206) and another communicating with the outer shield 224 of the output connector 220 (at the output end 208). As shown in FIG. 2, for each shielding structure 214A and 214B, the shielding structure capacitors 268 and the conductive elements 272 are arranged or centered on an offset axis that is at a radial distance from the central longitudinal axis 204 of the AC coupler 200. The shielding structure capacitors 268 and the conductive elements 272 of each shielding structure 214A and 214B may be supported on a planar outer dielectric substrate 276 (e.g., a first outer dielectric substrate 276A and a second outer dielectric substrate 276B in the illustrated embodiment) composed of a suitable dielectric material such as those noted above. The shielding structure capacitors 268 may be mounted on the surfaces of the shielding structures 214A and 214B facing the signal conductor 212. Deviations in ground plane geometry from an ideal ground plane cause less disturbance in impedance than similar geometric deviations in the signal conductor 212. Hence, the shielding structure capacitors 268 need not be mounted in openings in the shielding structures 214A and 214B, although they may be mounted in openings in some embodiments. The shielding structure capacitors 268 may include capacitors connected in series and/or capacitors connected in parallel.

In other embodiments, the shielding structure 214 (or the first shielding structure 214A and the second shielding structure 214B) may not include shielding structure capacitors 268 and instead include only a single conductive element extending continuously between the input end 206 and the output end 208.

The width (z-axis) of the shielding structure 214 (or the width of each shielding structure 214A and 214B in the illustrated embodiment) may be defined by the width of the shielding structure capacitors 268 (or the width of the conductive element 258 if shielding structure capacitors 268 are not included). In FIG. 7A, the width of the shielding structure capacitors 268 is indicated at 744. The width 744 of the shielding structure capacitors 268 may be compared to the width 444 (FIG. 4A) of the signal conductor capacitors 230 that defines the width of the signal conductor 212. According to the present disclosure, the width of each shielding structure 214A and 214B (e.g., the width 744 of the shielding structure capacitors 268) is substantially greater than the width of the signal conductor 212 (e.g., the width 444 of the signal conductor capacitors 230). By this configuration, the fields and currents in the AC coupler 200 may be very close to those in a similar transmission line having infinitely wide ground planes. Moreover, by making the width of the shielding structures 214A and 214B substantially greater than the width of the signal conductor 212, any external object that touches the outer shield 224 of the input connector or output connector, or the outside surfaces of the shielding structures 214A and 214B, or the edges of the shielding structures 214A and 214B, will cause negligible disturbances in characteristic impedance. In some embodiments, the width of the shielding structure 214 is at least 1.5 times (1.5×, or 150%) the width of the signal conductor 212. In other embodiments, the width of the shielding structure 214 is in a range from 1.5 to 6 times (1.5× to 6×, or 150% to 600%) the width of the signal conductor 212. In other embodiments, the width of the shielding structure 214 is at least 3 times (3×, or 300%) the width of the signal conductor 212. In other embodiments, the width of the shielding structure 214 is in a range from 3 to 4 times (3× to 4×, or 300% to 400%) greater than the width of the signal conductor 212.

In the present context, the widths of supporting dielectric substrates (e.g., central dielectric substrate 238 and outer dielectric substrates 276A and 276B) are not part of the consideration of the signal conductor width 444 and the shielding structure width 744. As shown in FIG. 2, for example, the widths of the central dielectric substrate 238 and outer dielectric substrates 276A and 276B may be the same or similar, and may be significantly greater than both the signal conductor width 444 and the shielding structure width 744.

In the present embodiment as best shown in FIG. 7A, each shielding structure capacitor 268 is realized by a pair of individual shielding structure capacitors 268A and 268B that are spatially parallel to each other, resulting in a first row of axially spaced shielding structure capacitors 268A and a second row of axially spaced shielding structure capacitors 268B. The individual shielding structure capacitors 268A and 268B of each pair may also be electrically connected in parallel across the center line of the shielding structure 214A or 214B. In some embodiments, the width of each individual shielding structure capacitor 268A and 268B is greater than the width 444 (FIG. 4A) of the signal conductor capacitors 230, resulting in the total width 744 of each shielding structure capacitor 268 (i.e., widths of the two individual shielding structure capacitors 268A and 268B plus the gap between them along the z-axis) being substantially greater than the width 444 of the signal conductor capacitors 230. As one non-limiting example, the width of each individual shielding structure capacitor 268A and 268B may be approximately twice the width 444 of the signal conductor capacitors 230, resulting in the total width 744 of each shielding structure capacitor 268 being approximately 4 times (4×, or 400%) the width 444 of the signal conductor capacitors 230.

In further embodiments, the width of the shielding structure 214 may exceed the width of the signal conductor 212 by a distance that is substantially greater than the offset distance (along the y-axis) between the signal conductor 212 and the shielding structure 214. Stated in another way, the difference between the width of the shielding structure 214 and the width of the signal conductor 212 is substantially greater than this offset distance. In the context of the present disclosure, the offset distance between the signal conductor 212 and the shielding structure 214 is taken to be the distance between the face of a signal conductor capacitor 230 and the closest face of a shielding structure capacitor 268. An example of this offset distance is illustrated in FIG. 4B. In FIG. 4B, a dashed line 414A indicates the elevation along the z-axis (or transverse x-y plane) at which the faces of the shielding structure capacitors 268 (the faces closest to the signal conductor capacitor 230) of the first shielding structure 214A are located. Similarly, a dashed line 414B indicates the elevation along the z-axis (or transverse x-y plane) at which the faces (the faces closest to the signal conductor capacitor 230) of the shielding structure capacitors 268 of the second shielding structure 214B are located. The offset distances are indicated at 244 in FIG. 4B. In some embodiments, the width of the shielding structure 214 (e.g., the width 744 of the shielding structure capacitors 268) exceeds the width of the signal conductor 212 by at least 2 times (2×) the offset distance 244. In other embodiments, the width of the shielding structure 214 less the width of the signal conductor 212 is in a range from 2 to 10 times (2× to 10×) the offset distance 244.

For embodiments in which the shielding structures (e.g., first shielding structure 214A and second shielding structure 214B) do not include capacitors, the offset distance between the signal conductor 212 and the shielding structure 214 may be taken to be the distance between the face of a signal conductor capacitor 230 and the closest face of the conductive element of the shielding structure.

The AC coupler 200 may include an impedance adjustment (or tuning) mechanism, i.e., a mechanism configured to enable a manufacturer or end user to adjust the characteristic impedance of the transmission line and thus compensate for variations in impedance caused by the components and dimensions of the AC coupler 200. In some embodiments, the impedance adjustment mechanism may be configured to enable a user to move the shielding structures 214A and 214B relative to the signal conductor 212, such as to adjust the distances (e.g., offset distance 244) between the shielding structures 214A and 214B and the signal conductor 212. The shielding structures 214A and 214B may generally be electrically coupled to the outer shields 224 of the coaxial input and output connectors by any electrical interconnecting structure. To accommodate adjusting the positions of the shielding structures 214A and 214B relative to the signal conductor 212, such interconnecting structures may be flexible or extendible components in some embodiments.

In the embodiment illustrated in FIGS. 2 and 3, the AC coupler 200 includes respective flanges or plates 280 at the input end 206 and the output end 208 configured for supporting and fixing the positions of the signal conductor 212 and the shielding structures 214A and 214B relative to the coaxial input and output connectors 218 and 220. In some embodiments, the flanges 280 may be integrated with the coaxial input and output connectors 218 and 220. The position of the signal conductor 212 may be fixed by mechanically coupling the axial ends of the central dielectric substrate 238 to the respective flanges 280. For example, as illustrated in FIGS. 2 and 3, tabs or extensions 282 of the central dielectric substrate 238 may be inserted into corresponding openings (notches, recesses, holes, grooves, etc.) 284 formed in the flanges 280. The axial ends of the shielding structures 214A and 214B may be mechanically coupled to the flanges 280 in an adjustable yet fixable (e.g., lockable) manner. For example, as illustrated, the shielding structures 214A and 214B may include metal bars or blocks 288 at their respective axial ends. The metal bars 288 may be configured to provide both electrical interconnections between the conductive elements 272 of the shielding structures 214A and 214B and the outer shields 224 (FIG. 3) of the coaxial input and output connectors 218 and 220, and mechanical connections between the outer dielectric substrates 276A and 276B and the flanges 280. Adjustment members 290, for example fastening components (e.g., screws, bolts, or the like) pass through vertically (y-axis) oriented slots 292 formed through the flanges 280 and into contact with the outer dielectric substrates 276A and 276B or with the metal bars 288 if provided (such as into holes or open grooves of the metal bars 288). By this configuration, the shielding structures 214A and 214B are slidable toward and away from the signal conductor 212. Once the desired offset distance 244 is attained between the shielding structures 214A and 214B and the signal conductor 212, the positions of the shielding structures 214A and 214B may be fixed by tightening or clamping the adjustment members 290 against the flanges 280. Depending on the embodiment, the adjustment members 290 may be components integral with or separate from the outer dielectric substrates 276A and 276B. All three dielectric substrates 238, 276A, and 276B may be made wide enough to allow the adjustment mechanism to set the distances between the planes without disturbing the impedance of the transmission line, thereby enabling simultaneous adjustment and monitoring of the impedance of the transmission line. In the illustrated embodiment, the metal bars 288 and flanges 280 provide an electrical signal path between the conductive elements 272 of the shielding structures 214A and 214B and the outer shields 224 and the outer shields 224 of the coaxial input and output connectors 218 and 220.

In some embodiments, the axial end regions of the signal conductor 212 and/or the axial end regions of the shielding structures 214A and 214B are, or include, structural transitions that may be optimized to minimize the reflections that would result from direct connections at the input end 206 and the output end 208 between the planar geometries of the signal conductor 212 and shielding structures 214A and 214B and the coaxial input and output connectors 218 and 220. The axial end regions are the regions between the coaxial input and output connectors 218 and 220 and the sections of the signal conductor 212 and/or shielding structures 214A and 214B featuring uniform geometry (i.e., the repeating pattern of capacitors and conductive elements). The structural transitions may incorporate changes in the geometry of the signal conductor 212 and/or shielding structures 214A and 214B. The structural transitions may have tapered or stepped geometries as needed for providing optimal broadband impedance matching. FIG. 2 illustrates one example of stepped structural transitions, which include gaps 258 formed in the central dielectric substrate 238 at the axial ends, between the signal conductor 212 and the coaxial connectors 218 and 220 (only the gap 258 at the input end 206 is visible in FIG. 2). The center conductors 222 (FIG. 3) of the coaxial connectors 218 and 220 are exposed in the gaps 258. Similarly, FIG. 5A illustrates an example of stepped structural transitions 554, which include gaps 558 at the axial ends of the central dielectric substrate 538. In the case of the shielding structures 214A and 214B, the structural transitions may be incorporated into the metal bars 288. On the other hand, the dimensions and shape of the metal bars 288 may be chosen so as to extend the repeated pattern of height variations of the shielding structures 214A and 214B due to alternation of the shielding structure capacitors 268 and the conductive elements 272. In such case, the impedance discontinuity at the transition between the metal bars 288 and the shielding structure capacitors 268 may be reduced. In some embodiments, dielectric material may be added or removed in the transition regions to minimize reflections.

As described above, in various embodiments the signal conductor 212, or both the signal conductor 212 and the shielding structures 214A and 214B, may include more than one DC blocking capacitor. Multiple capacitors connected in series are useful for withstanding the high voltage applied across the AC coupler 200. However, the applied voltage may not divide evenly among the capacitors due to variations in leakage resistance from one capacitor to the next. One way to force uniform division of the applied voltage is to shunt the capacitors with equal-value balancing resistors whose resistance is low enough to swamp the variations in leakage resistance but high enough to avoid excessive DC current through the AC coupler 200. As one non-limiting example, the resistance may be about 1 GΩ. In some embodiments and as illustrated in FIGS. 2 and 7B, balancing resistors 210 are mounted on the outer dielectric substrate 276 (i.e., each outer dielectric substrate 276A and 276B) and coupled in shunt relation to the shielding structure capacitors 268, such as through a pattern of transversely-oriented (along the z-axis) conductive strips 216 on the surface of the outer dielectric substrate 276 and conductive wires or pins through the thickness of the outer dielectric substrate 276.

It may be preferable to position such balancing resistors 210 on the side of the outer dielectric substrate 276A or 276B opposite to the side on which the associated shielding structure capacitors 268 are mounted to minimize the effect of the balancing resistors 210 on the high-frequency characteristics of the transmission line. As long as the same number of shielding structure capacitors 268 are utilized in both shielding structures 214A and 214B, a single set of balancing resistors 210 may be shared between the shielding structures 214A and 214B by connecting the corresponding junctions of the shielding structure capacitors 268 together between the two planes.

According to another aspect of the present disclosure, the signal conductor capacitors 230 may share the same set of balancing resistors (e.g., balancing resistors 210) with the shielding structure capacitors 268 assuming, again, equal numbers of series capacitors. In this case, the signal conductor capacitors 230 need to be isolated from the ground plane connections, such as by providing other resistors 228 (FIGS. 2, 4A and 4B), which may be of moderately high value (e.g., 10 MSΩ). Interconnections between associated resistors 210 and 228 positioned at different planes may be made, for example, via conductive pins or wires 232 (FIG. 2). Such pins or wires 232 may be soldered in place after setting the positions of the shielding structures 214A and 214B relative to the signal conductor 212 to adjust impedance. As best shown in FIG. 4A, if discrete balancing resistors 228 are utilized on the signal conductor 212, their effect on the AC performance of the transmission line may be minimized by breaking each resistor 228 into two or more small resistors connected in series by short, narrow conductors, and arranging the string of resistors close to and perpendicular to the signal conductor 212. This configuration minimizes the area of additional conductors close to the signal conductor 212, where the electric fields are highest.

As an alternative to discrete balancing resistors 228, thick film patterns may be deposited directly on the substrates that support the capacitors.

Depending on the solid dielectric materials employed, it may be desirable to increase leakage current path lengths in one or more of the dielectric substrates 238, 276A, and 276B. In some embodiments, leakage current path lengths are increased by providing geometric features. Geometric features may be formed by removing substrate material, such as by introducing slots or other type of openings in one or more of the dielectric substrates 238, 276A, and 276B. For example, as shown in FIG. 5A, the central dielectric substrate 538 may include a uniform or repeating pattern of inner slots 550 and outer slots 552. In the specific example illustrated, the inner slots 550 extend along the width of the dielectric substrate 538 from the openings 540 toward the outer lateral edges of the dielectric substrate 538, but do not reach the outer lateral edges of the dielectric substrate 538. The outer slots 552 extend from the outer lateral edges toward the central longitudinal axis of the dielectric substrate 538. Similarly, as best shown in FIG. 7B the outer dielectric substrate 276 may include a uniform or repeating pattern of transversely-oriented inner slots 750 and outer slots 752. Such slots may also serve to reduce the mechanical stress caused by the mismatch in thermal expansion between the capacitors and the substrate, and minimize the overall size of the AC coupler 200 for optimal high-frequency performance. Alternatively or additionally, geometric features may be formed by adding substrate material, such as by forming raised features (e.g., ribs, not shown) on one or more of the dielectric substrates 238, 276A, and 276B between high-voltage points. Like openings, raised features may be arranged in a uniform or repeating pattern. It will be understood that the slot patterns illustrated in FIGS. 5A and 7B are examples. Various other slot patterns may be implemented that are effective for increasing leakage current path lengths.

FIG. 8A is a circuit diagram of an example of a central signal conductor 812 according to some embodiments. FIG. 8B is a circuit diagram of an example of a shielding structure 814 according to some embodiments. The central signal conductor 812 generally includes a plurality of signal conductor capacitors 830 electrically coupled in series between an input end (node) 806 and an output end (node) 808, and the shielding structure 814 generally provides an electrical current return path and ground plane interconnected between the input end 806 and the output end 808. The central signal conductor 812 in combination with the shielding structure 814 forms a transmission line structure operable as an AC coupler that effectively transmits wideband AC signals from an AC input connector positioned at the input end 806 to an AC output connector positioned at the output end 808, while blocking DC and low-frequency signals as described above. As also described above, for this purpose the central signal conductor 812 is interconnected between the signal conducting portions of an AC input connector and an AC output connector, and the shielding structure 814 is interconnected between the shielding/grounding portions of the AC input connector and AC output connector. The transmission line structure may have a generally planar geometry with one or more shielding structures 814 provided, an example of which is described above and illustrated in FIG. 2. Alternatively, the transmission line structure may have a generally coaxial geometry with the shielding structure(s) 814 coaxially surrounding the central signal conductor 812, an example of which is described below. As a further alternative, the transmission line structure may include more than one central signal conductor 812, examples of which are described below.

The shielding structure 814 may include a plurality of shielding structure capacitors 868 connected in series between the input end 806 and the output end 808. Each shielding structure capacitor 868 may include a pair of parallel-connected shielding structure capacitors 868A and 868B as described above. In some implementations, a set of balancing resistors 810 may equalize the DC voltages across the individual capacitors 868A and 868B. As an alternative to a similar set of balancing resistors, the signal conductor 812 may include isolating resistors 828 connected between conductive elements (nodes 802), which interconnect the signal conductor capacitors 512, and common connection points or nodes labeled TP1, TP2, TP3, TP4, TP5, TP6, and TP7. Connecting these nodes TP1, TP2, TP3, TP4, TP5, TP6, and TP7 to the corresponding nodes of the shielding structure 814 (such as by conductive pins or wires as described above) forces the DC voltage drops across the signal conductor capacitors 830 to match the equalized DC voltages across the shielding structure capacitors 868. Each isolating resistor 828 may include two or more discrete series-connected resistors, as shown and as described above.

Figure 9:
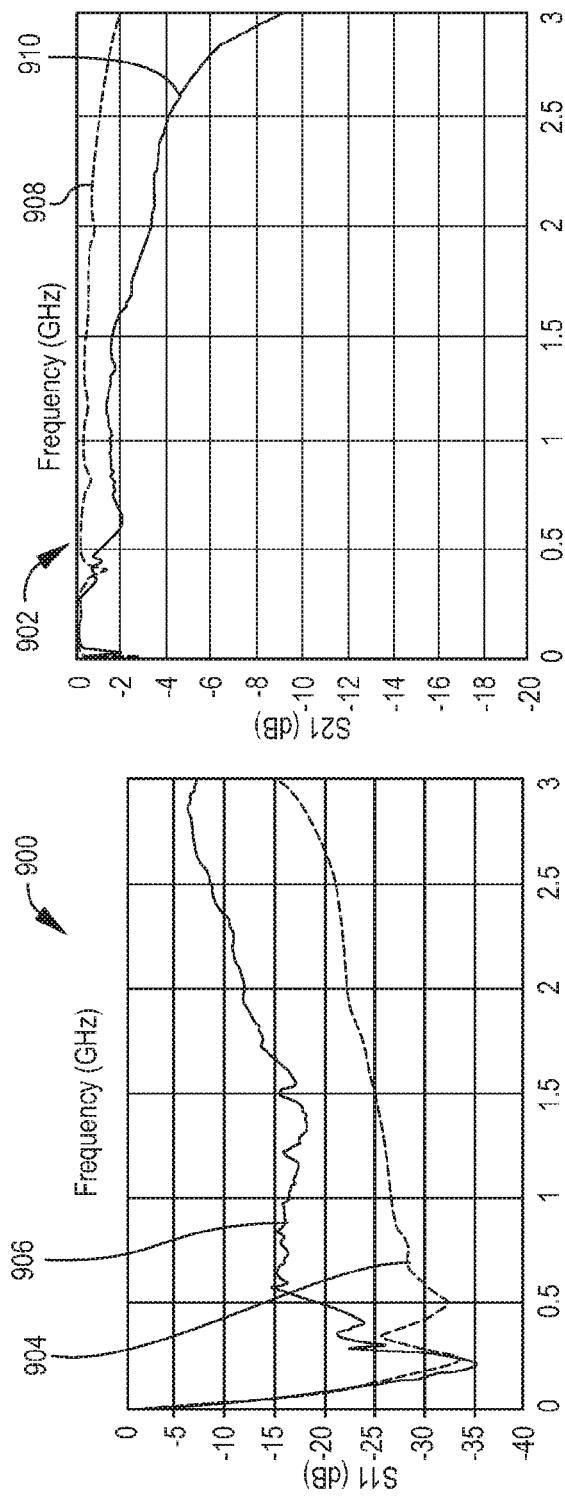
FIG. 9 is a set of graphs of measured scattering parameters (s-parameters) comparing the performance of an AC coupler as disclosed herein with the performance of a previously known AC coupler.

FIG. 9 is a set of graphs of measured scattering parameters (s-parameters) comparing the performance of an AC coupler as disclosed herein (for example, consistent with the embodiment illustrated in FIG. 2) with the performance of a previously known (prior-art) AC coupler (as described in the Background section of the present disclosure). The s-parameters are measured in decibels (dB) as a function of frequency (GHz). Specifically, FIG. 9 includes a graph 900 of the measured S11 parameter (input port voltage reflection coefficient) for the presently disclosed AC coupler (trace 904) and the previously known AC coupler (trace 906). FIG. 9 also includes a graph of the measured S21 parameter (forward voltage gain) for the presently disclosed AC coupler (trace 908) and the previously known AC coupler (trace 910). FIG. 9 demonstrates effective wideband operation of the presently disclosed AC coupler up to 3 GHz.

Figure 10:
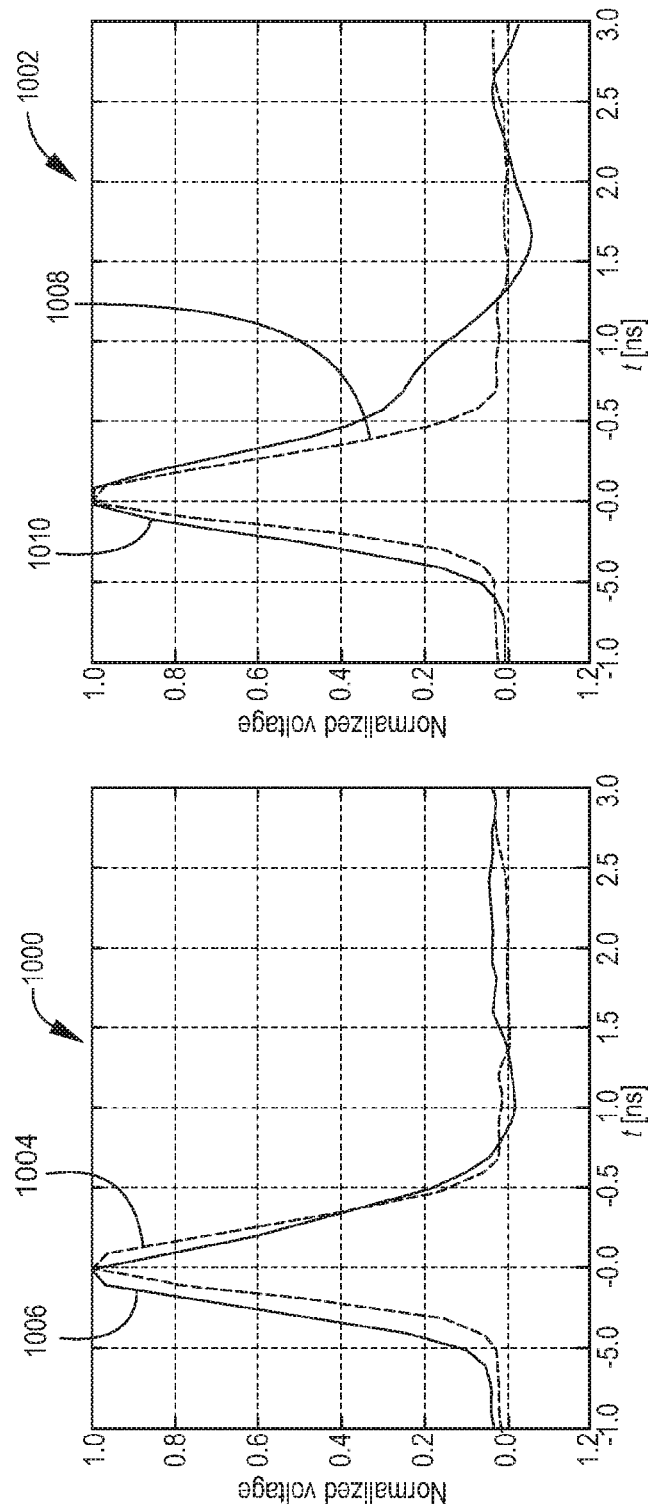
FIG. 10 is a set of graphs comparing the time-domain pulse response of an AC coupler as disclosed herein with the time-domain pulse response of a previously known AC coupler.

FIG. 10 is a set of graphs 1000 and 1002 illustrating the time-domain pulse response of an AC coupler as disclosed herein (for example, consistent with the embodiment illustrated in FIG. 2). In the first graph 1000, the pulse output of a representative TOFMS detector connected directly to the input of a high speed oscilloscope is labeled 1006. The detector output under the same conditions, but coupled through the presently disclosed AC coupler, is labeled 1004. In the second graph, the same pulse response of the presently disclosed AC coupler and the corresponding response of the previously known AC coupler are labeled 1008 and 1010, respectively. As shown, the side lobe is eliminated in the presently disclosed AC coupler and the output ripple is kept low.

Figure 11:
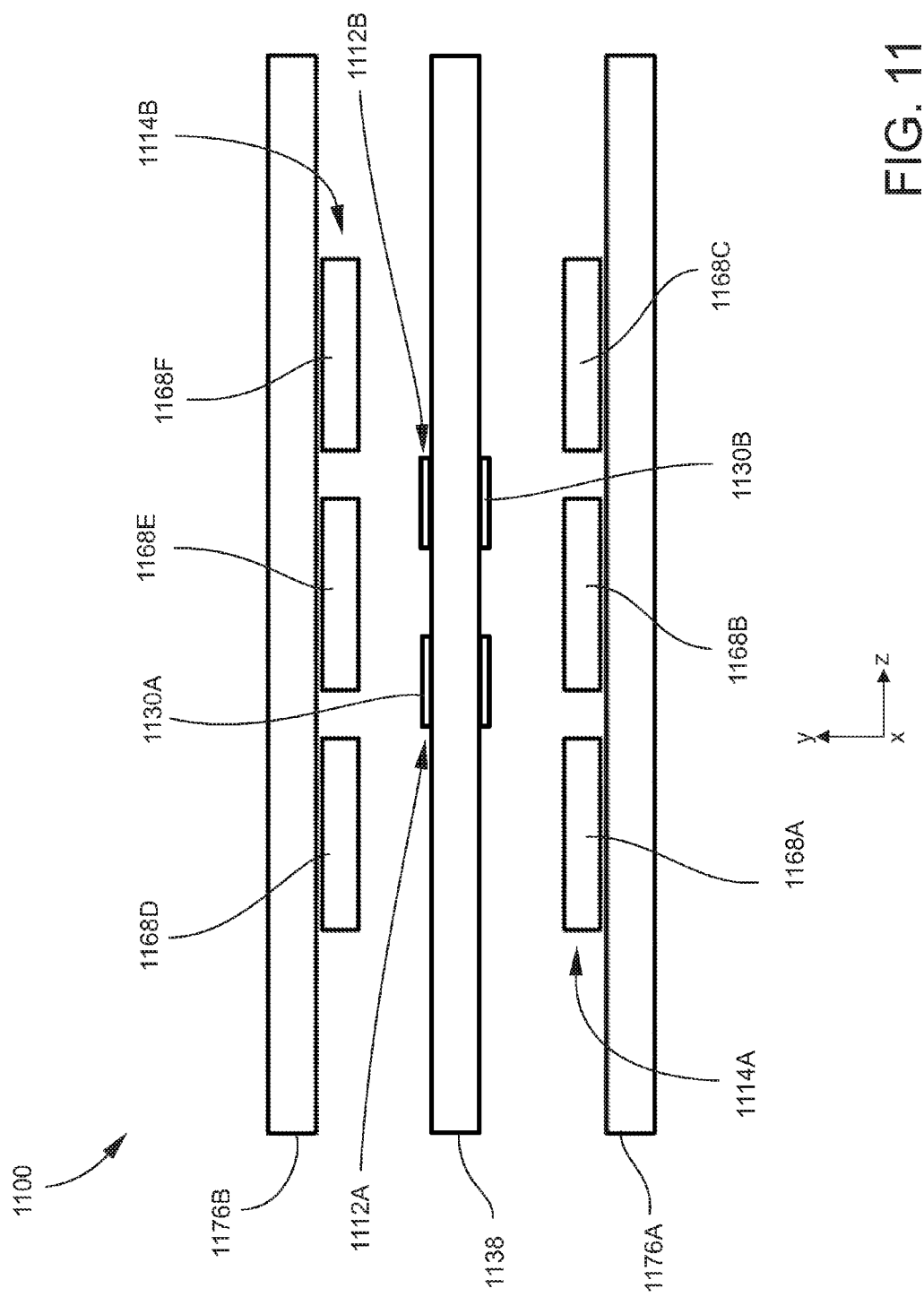
FIG. 11 is an axial end view of an example of an AC coupler according to another embodiment, in which a plurality of signal conductors are provided.

FIG. 11 is an axial end view of an example of an AC coupler 1100 according to another embodiment, in which a plurality of signal conductors are provided. In the specific example illustrated, the AC coupler 1100 includes two central (inner) signal conductors, a first central signal conductor 1112A and a second central signal conductor 1112B, positioned in a coplanar arrangement. The AC coupler 1100 also includes two outer shielding structures, a first outer shielding structure 1114A and a second outer shielding structure 1114B, positioned at respective offset distances from the signal conductors 1112A and 1112B on opposite sides of the signal conductors 1112A and 1112B. With this configuration, the AC coupler 1100 may be operated as a differential transmission line with the two signal conductors 1112A and 1112B driven 180 degrees out of phase. Alternatively, the two signal conductors 1112A and 1112B may be driven in phase with each other. The AC coupler 1100 may provide one or more of the advantages described above in regard to other embodiments.

Generally, the signal conductors 1112A and 1112B and outer shielding structures 1114A and 1114B may be configured similar to those described above in conjunction with FIGS. 2 to 7B, with appropriate electrical connections made to AC input and output connectors. Thus, the first signal conductor 1112A may include a plurality of first signal conductor capacitors 1130A, and the second signal conductor 1112B may include a plurality of second signal conductor capacitors 1130B. All of the signal conductor capacitors 1130A and 1130B may be supported by a central dielectric substrate 1138 common to both signal conductors 1112A and 1112B. The first outer shielding structure 1114A may include a plurality of shielding structure capacitors 1168A, 1168B, and 1168C, which may be supported by a first outer dielectric substrate 1176A. Likewise, the second outer shielding structure 1114B may include a plurality of shielding structure capacitors 1168D, 1168E, and 1168F, which may be supported by a second outer dielectric substrate 1176B.

Figure 12:
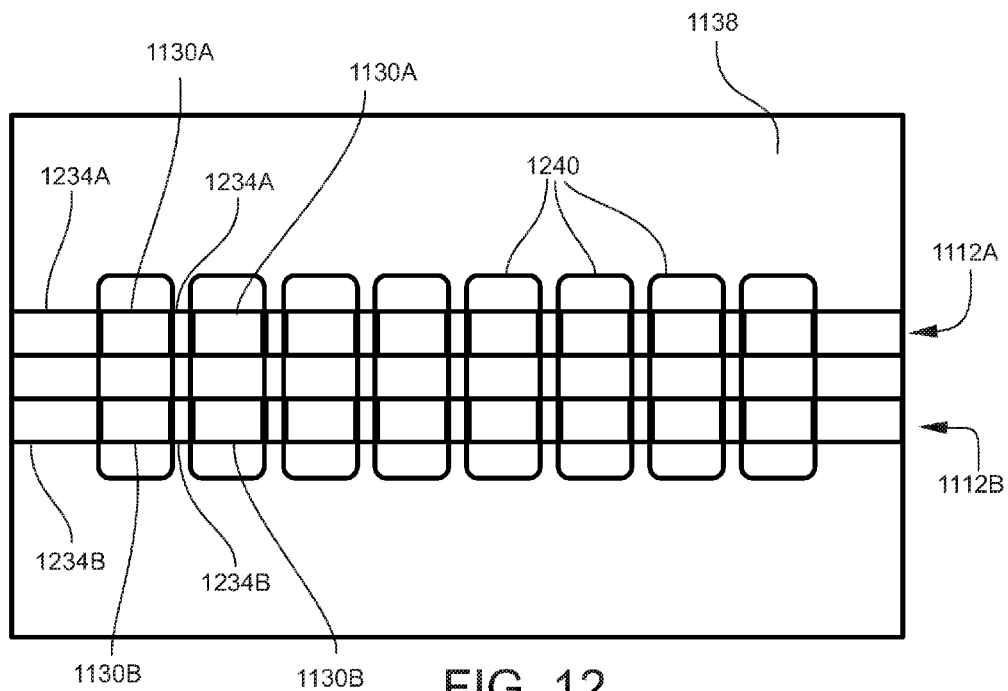
FIG. 12 is a plan view of an example of central signal conductors and an associated central dielectric substrate that may be provided in the AC coupler illustrated in FIG. 11.

FIG. 12 is a plan view of an example of the signal conductors 1112A and 1112B and associated central dielectric substrate 1138. The signal conductors 1112A and 1112B include respective arrays of signal conductor capacitors 1130A and 1130B between the input end and the output end of the AC coupler 1100. Adjacent signal conductor capacitors 1130A and 1130B are interconnected by respective conductive elements 1234A and 1234B, with conductive elements 1234A and 1234B at the axial ends being available for electrical communication with AC input and output connectors. In the present embodiment, the signal conductor capacitors 1130A and 1130B are positioned in openings 1240 formed in the central dielectric substrate 1138 such that the signal conductor capacitors 1130A and 1130B are coplanar or substantially coplanar with the central dielectric substrate 1138, as described above. In the present embodiment, each opening is wide enough to accommodate one signal conductor capacitor 1130A and one adjacent signal conductor capacitor 1130B. In other embodiments, each of the first signal conductor capacitors 1130A and each of the signal conductor capacitors 1130B may be replaced with a pair of capacitors on opposing sides of the central dielectric substrate 1138, as described above in conjunction with FIG. 6. Moreover, as also described above, in some embodiments each of the first signal conductor capacitors 1130A and each of the second signal conductor capacitors 1130B may be replaced with two or more capacitors arranged side-by-side along the width of the central dielectric substrate 1138.

Figure 13:
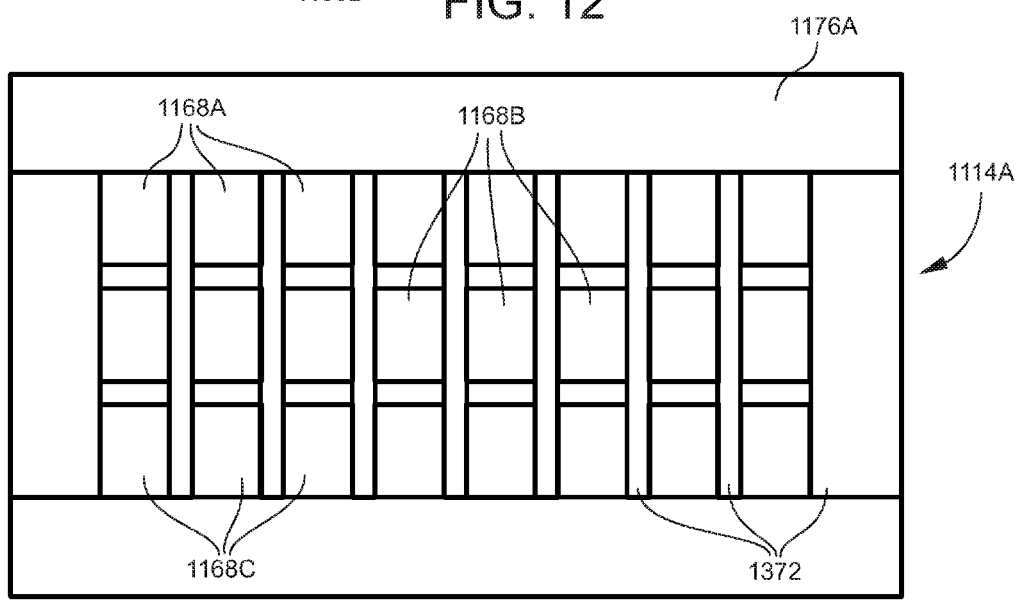
FIG. 13 is a plan view of an example of an outer shielding structure and associated first outer dielectric substrate that may be provided in the AC coupler illustrated in FIG. 11.

FIG. 13 is a plan view of an example of the first outer shielding structure 1114A and associated first outer dielectric substrate 1176A, with the understanding that the second outer shielding structure 1114B and second outer dielectric substrate 1176B may be configured the same or similarly. The first outer shielding structure 1114A includes respective arrays of shielding structure capacitors 1168A, 1168B, and 1168C between the input end and the output end of the AC coupler 1100. Other embodiments may include more or less than three arrays of capacitors. Adjacent shielding structure capacitors 1168A, 1168B, and 1168C are interconnected by respective conductive elements 1372, with conductive elements 1372 at the axial ends being available for electrical communication with AC input and output connectors.

As in other embodiments described above, the width of each shielding structure 1114A and 1114B is substantially greater than the width of the signal conductor, where "substantially greater" again may be quantified by the examples of ranges specified above for the relative widths of the signal conductor and shielding structure. In the present embodiment, the width of the signal conductor is the total width occupied by the two coplanar signal conductors 1112A and 1112B, which is dictated by the widths of the signal conductor capacitors 1130A and 1130B plus the gap between them. Likewise in the present embodiment, the width of each shielding structure 1114A and 1114B is the total width occupied by the shielding structure capacitors 1168A, 1168B, and 1168C (or the shielding structure capacitors 1168D, 1168E, and 1168F) plus the gaps between them.

In further embodiments and as also described above, the width of each shielding structure 1114A and 1114B may be substantially greater than the offset spacing (again, in the direction orthogonal to the longitudinal axis) between the coplanar signal conductors 1112A and 1112B and each shielding structure 1114A and 1114B. In this aspect, "substantially greater" again may be quantified by the examples of ranges specified above for the offset spacing.

Figure 14:
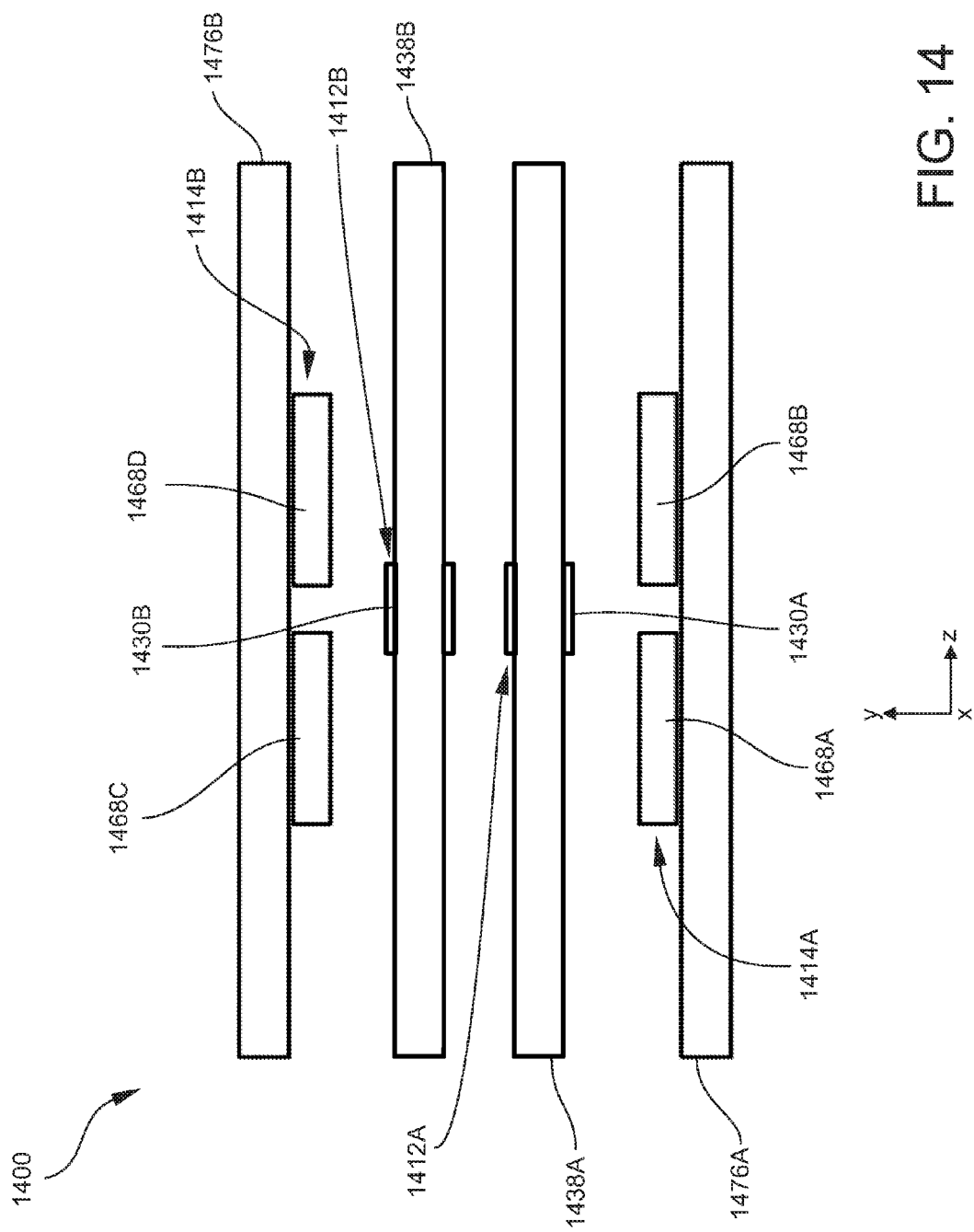
FIG. 14 is an axial end view of an example of an AC coupler according to another embodiment, in which a plurality of signal conductors are provided.

FIG. 14 is an axial end view of an example of an AC coupler 1400 according to another embodiment, in which a plurality of signal conductors are provided. In the specific example illustrated, the AC coupler 1400 includes two central (inner) signal conductors, a first central signal conductor 1412A and a second central signal conductor 1212B positioned in a broadside, or spatially parallel, arrangement. The AC coupler 1400 also includes two outer shielding structures, a first outer shielding structure 1414A and a second outer shielding structure 1414B, positioned at respective offset distances from the outer sides (facing away from the central longitudinal axis of the AC coupler 1400) of the signal conductors 1412A and 1412B. With this configuration, the AC coupler 1400 may be operated as a differential transmission line with the two signal conductors 1412A and 1412B driven 180 degrees out of phase. Alternatively, the two signal conductors 1412A and 1412B may be driven in phase with each other. The AC coupler 1400 may provide one or more of the advantages described above in regard to other embodiments.

Generally, the signal conductors 1412A and 1412B and outer shielding structures 1414A and 1414B may be configured similar to those described above in conjunction with FIGS. 2 to 7B, with appropriate electrical connections made to AC input and output connectors. Thus, the first signal conductor 1412A may include a plurality of first signal conductor capacitors 1430A, and the second signal conductor 1412B may include a plurality of second signal conductor capacitors 1430B. The first signal conductor capacitors 1430A and associated conductive elements (not shown) may be supported by a first central (inner) dielectric substrate 1438A. Likewise, the second signal conductor capacitors 1430B and associated conductive elements (not shown) may be supported by a second central (inner) dielectric substrate 1438B, which is separated from the first central dielectric substrate 1438A along the radial offset direction. Thus, the signal conductors 1412A and 1412B (and associated central dielectric substrates 1438A and 1438B) are each spaced from the central longitudinal axis of the AC coupler 1400 by a distance along the radial offset direction.

The first outer shielding structure 1414A may include a plurality of shielding structure capacitors 1468A and 1468B, which may be supported by a first outer dielectric substrate 1476A along with associated conductive elements (not shown). Likewise, the second outer shielding structure 1414B may include a plurality of shielding structure capacitors 1468C and 1468D, which may be supported by a second outer dielectric substrate 1476B along with associated conductive elements (not shown).

The signal conductor capacitors 1430A and 1430B and the shielding structure capacitors 1468A, 1468B, 1468C, and 1468D may be arranged and interconnected between the input and output ends of the AC coupler 1400 according to any of the configurations disclosed herein. In the present embodiment, the signal conductor capacitors 1430A and 1430B are positioned in openings (not shown) formed in the respective central dielectric substrates 1438A and 1438B such that the signal conductor capacitors 1430A and 1430B are coplanar or substantially coplanar with the respective central dielectric substrates 1438A and 1438B, as described above. In other embodiments, each of the first signal conductor capacitors 1430A and each of the second signal conductor capacitors 1430B may be replaced with a pair of capacitors on opposing sides of the central dielectric substrates 1438A and 1438B, respectively, as described above in conjunction with FIG. 6. Moreover, as also described above, in some embodiments each of the first signal conductor capacitors 1430A and each of the second signal conductor capacitors 1430B may be replaced with two or more capacitors arranged side-by-side along the width of the central dielectric substrates 1438A and 1438B, respectively. In the present embodiment, the shielding structures 1414A and 1414B each include two side-by-side arrays of capacitors (shielding structure capacitors 1468A and 1468B, and shielding structure capacitors 1468C and 1468D, respectively). Other embodiments, however, may include more or less than two arrays of capacitors.

As in other embodiments described above, the width of each shielding structure 1414A and 1414B is substantially greater than the width of each signal conductor 1412A and 1412B, where "substantially greater" again may be quantified by the examples of ranges specified above for the relative widths of the signal conductor and shielding structure. In the present embodiment, the widths of the signal conductors 1412A and 1412B are dictated by the respective widths of the signal conductor capacitors 1430A and 1430B. The width of each shielding structure 1414A and 1414B is the total width occupied by the shielding structure capacitors 1468A and 1468B (or the shielding structure capacitors 1468C and 1468D) plus the gaps between them.

In further embodiments and as also described above, the width of the first shielding structure 1414A may be substantially greater than the offset spacing (again, in the direction orthogonal to the longitudinal axis) between the first signal conductor 1412A and the first shielding structure 1414A. Likewise, the width of the second shielding structure 1414B may be substantially greater than the offset spacing between the second signal conductor 1412B and the second shielding structure 1414B. In this aspect, "substantially greater" again may be quantified by the examples of ranges specified above for the offset spacing.

Figure 15:
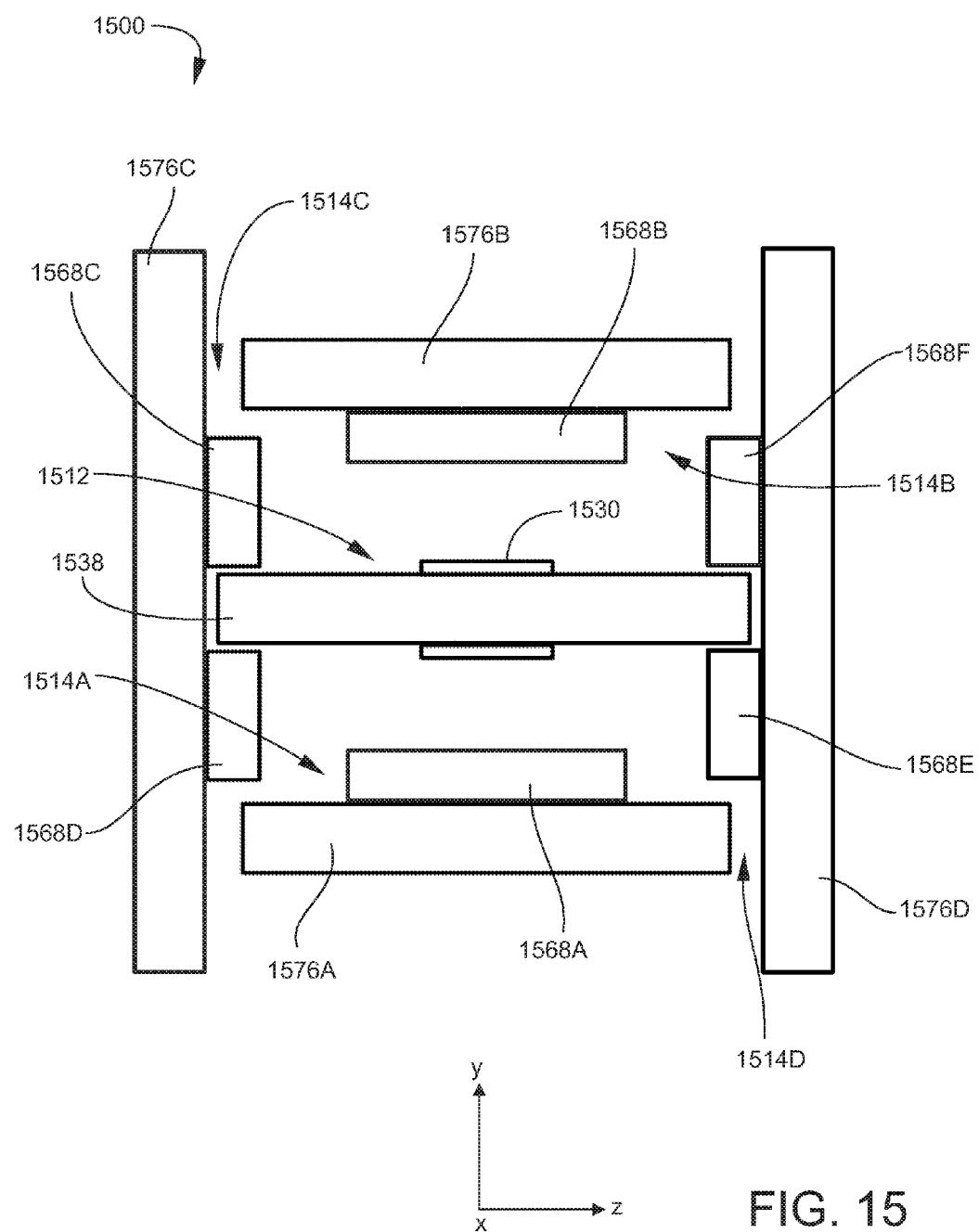
FIG. 15 is an axial end view of an example of an AC coupler according to another embodiment, in which the AC coupler has a coaxial, prismatic geometry.

FIG. 15 is an axial end view of an example of an AC coupler 1500 according to another embodiment. The AC coupler 1500 has a prismatic coaxial geometry. Specifically, the AC coupler 1500 has a rectangular cross-section, and may be assembled from planar structures as shown. In the example illustrated, the AC coupler 1500 includes a central (inner) signal conductor 1512 surrounded by a plurality of outer shielding structures, specifically a first (bottom) outer shielding structure 1514A, a second (top) outer shielding structure 1514B, a third (side) outer shielding structure 1514C, and a fourth (side) outer shielding structure 1514D. The first outer shielding structure 1514A and the second outer shielding structure 1514B are spatially parallel to each other and to the central signal conductor 1512, and are positioned at respective offset distances (y-axis) from the signal conductor 1512 on opposite sides of the signal conductor 1512. The third outer shielding structure 1514C and the fourth outer shielding structure 1514D are spatially parallel to each other and spaced from each other by a distance along the transverse direction (z-axis). Hence, the third outer shielding structure 1514C and the fourth outer shielding structure 1514D are oriented orthogonal relative to the central signal conductor 1512, the first outer shielding structure 1514A, and the second outer shielding structure 1514B. The outer shielding structures 1514A, 1514B, 1514C, and 1514D may be considered as collectively forming an outer shielding structure of coaxial geometry that surrounds the centrally-positioned signal conductor 1512. The AC coupler 1500 may provide one or more of the advantages described above in regard to other embodiments.

Generally, the signal conductor 1512 and outer shielding structures 1514A, 1514B, 1514C, and 1514D may be configured similar to those described above in conjunction with FIGS. 2 to 7B, with appropriate electrical connections made to AC input and output connectors. Thus, the signal conductor 1512 may include a plurality of signal conductor capacitors 1530, which may be supported by a central dielectric substrate 1538. The first outer shielding structure 1514A may include a plurality of shielding structure capacitors 1568A, which may be supported by a first outer dielectric substrate 1576A. Likewise, the second outer shielding structure 1514B may include a plurality of shielding structure capacitors 1568B, which may be supported by a second outer dielectric substrate 1576B. The third outer shielding structure 1514C may include a plurality of shielding structure capacitors 1568C and 1568D, which may be supported by a third outer dielectric substrate 1576C. Likewise, the fourth outer shielding structure 1514D may include a plurality of shielding structure capacitors 1568E and 1568F, which may be supported by a fourth outer dielectric substrate 1576D.

Figure 16:
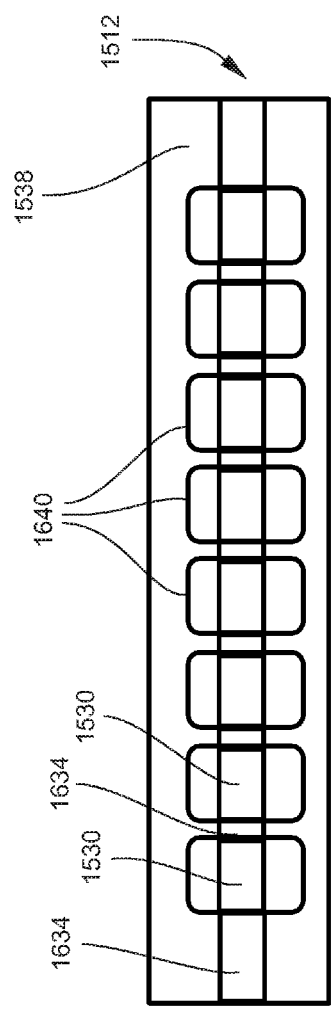
FIG. 16 is a plan view of an example of a central signal conductor and associated central dielectric substrate that may be provided in the AC coupler illustrated in FIG. 15.

FIG. 16 is a plan view of an example of the central signal conductor 1512 and associated central dielectric substrate 1538. The signal conductor 1512 includes an array of signal conductor capacitors 1530 between the input end and the output end of the AC coupler 1500. Adjacent signal conductor capacitors 1530 are interconnected by conductive elements 1634, with conductive elements 1634 at the axial ends being available for electrical communication with AC input and output connectors. In the present embodiment, the signal conductor capacitors 1530 are positioned in openings 1640 formed in the central dielectric substrate 1538 such that the signal conductor capacitors 1530 are coplanar or substantially coplanar with the central dielectric substrate 1538, as described above. In other embodiments, each of the signal conductor capacitors 1530 may be replaced with a pair of capacitors on opposing sides of the central dielectric substrate 1538, as described above in conjunction with FIG. 6. Moreover, as also described above, in some embodiments each of the signal conductor capacitors 1530 may be replaced with two or more capacitors arranged side-by-side along the width of the central dielectric substrate 1538.

Figure 17:
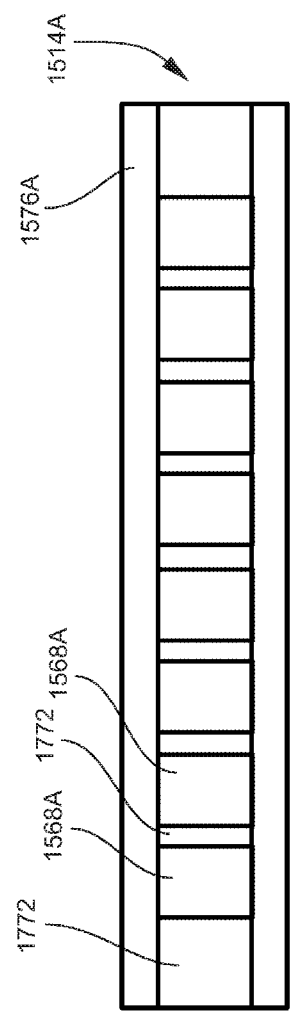
FIG. 17 is a plan view of an example of an outer shielding structure and associated outer dielectric substrate that may be provided in the AC coupler illustrated in FIG. 15.

FIG. 17 is a plan view of an example of the first outer shielding structure 1514A and associated first outer dielectric substrate 1576A, with the understanding that the second outer shielding structure 1514B and second outer dielectric substrate 1576B may be configured the same or similarly. The first outer shielding structure 1514A includes an array of shielding structure capacitors 1568A between the input end and the output end of the AC coupler 1500. Other embodiments may include more than one array of capacitors, as described above. Adjacent shielding structure capacitors 1568A are interconnected by respective conductive elements 1772, with conductive elements 1772 at the axial ends being available for electrical communication with AC input and output connectors.

Figure 18:
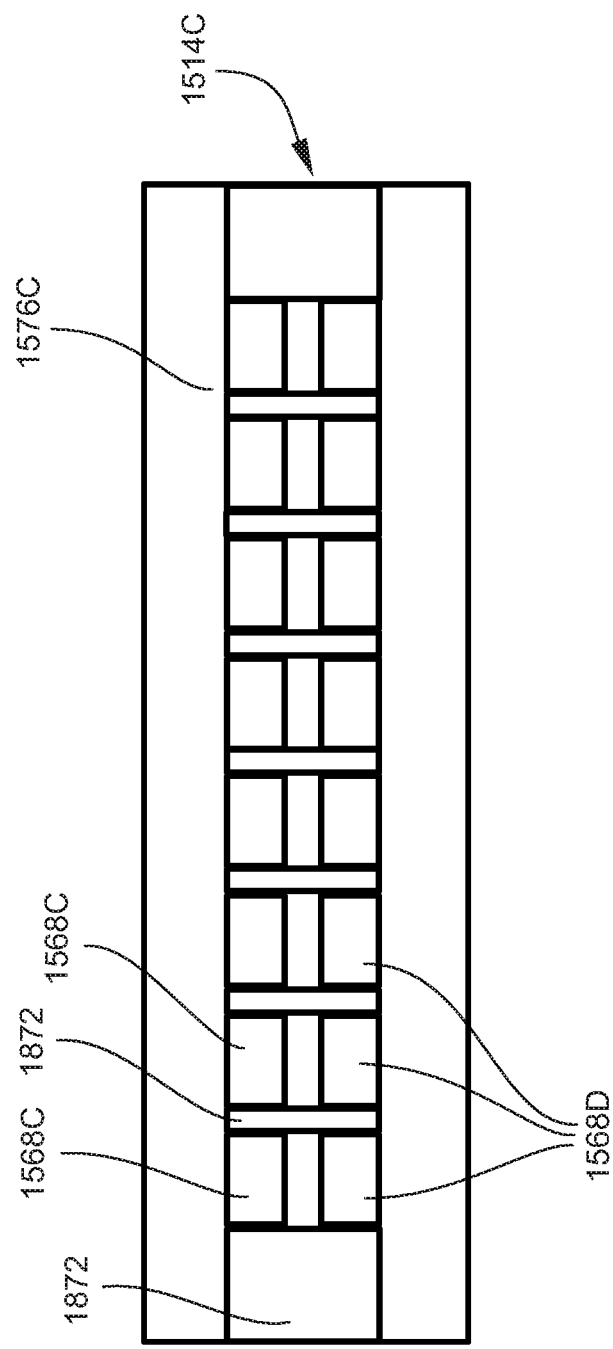
FIG. 18 is a plan view of an example of another outer shielding structure and associated outer dielectric substrate that may be provided in the AC coupler illustrated in FIG. 15.

FIG. 18 is a plan view of an example of the third outer shielding structure 1514C and associated first outer dielectric substrate 1576C, with the understanding that the fourth outer shielding structure 1514D and fourth outer dielectric substrate 1576D may be configured the same or similarly. The third outer shielding structure 1514C includes respective arrays of shielding structure capacitors 1568C and 1568D between the input end and the output end of the AC coupler 1500. Other embodiments may include more or less than two arrays of capacitors. Adjacent shielding structure capacitors 1568C and 1568D are interconnected by conductive elements 1872, with conductive elements 1872 at the axial ends being available for electrical communication with AC input and output connectors.

In some embodiments, the AC coupler 1500 is configured such that the elevations positions (y-axis) of the first and second shielding structures 1514A and 1514B relative to the signal conductor 1512 can be varied so as to adjust impedance. For this purpose, the AC coupler 1500 may include adjustment mechanisms at the input end and output end such as described above. For example, the first and second shielding structures 1514A and 1514B may be attached to AC input and output connectors through outer adjustable metal bars, while the third and fourth outer shielding structures 1514C and 1514D are attached through fixed metal bars.

Referring to FIG. 15, when the outer shielding structures parallel to the signal conductor 1512 (i.e., the first and second outer shielding structures 1514A and 1514B) are substantially wider than the signal conductor 1512, the gaps between the various outer shielding structures provided (i.e., the outer shielding structures 1514A, 1514B, 1514C and 1514D) are not significant. As the outer shielding structures become smaller, narrower gaps may be required to prevent field leakage and degraded performance. As the outer shielding structures become even smaller, the outer shielding structures may need to overlap each other, as illustrated in the example of FIG. 15. For example, the first and second outer dielectric substrates 1576A and 1576B may be positioned within the footprint (x-y plane) of the third and fourth outer dielectric substrates 1576C and 1576D. Also, the central dielectric substrate 1538 may extend into the gap between the shielding structure capacitors 1568C and 1568D and the gap between the shielding structure capacitors 1568E and 1568F. The first and second outer shielding structures 1514A and 1514B may be secured to the orthogonal third and fourth outer shielding structures 1514C and 1514D to provide mechanical stability after adjusting impedance. The first and second outer shielding structures 1514A and 1514B may also be electrically connected to the third and fourth outer shielding structures 1514C and 1514D, which may facilitate providing a network of balancing and isolating resistors in a manner similar to that described above in other embodiments.

In other embodiments, an AC coupler with coaxial geometry may include a plurality of distinct signal conductors, driven 180 degrees out of phase or in-phase with each other. In still other embodiments, an AC coupler with coaxial geometry be realized by signal conductor(s) and shielding structure(s) having cylindrical and/or arcuate structures instead of planar structures, or a combination of cylindrical, arcuate and/or planar structures.

In various embodiments, AC couplers such as the AC coupler 1100, 1400, and 1500 may include one or more other features described above in conjunction with the other embodiments and illustrated in FIGS. 2 to 8B. Such other features include, for example, balancing resistors, isolating resistors, metal bars and/or flanges providing mechanical support and/or electrical connections at the input and output ends, adjustment mechanisms to adjust the positions of one or more of the shielding structures, transitional regions, slots and/or ribs formed on or in the dielectric substrates, etc.

Exemplary Embodiments

Exemplary embodiments provided in accordance with the presently disclosed subject matter include, but are not limited to, the following:

1. An AC coupler for transmitting high-frequency components of a wideband signal, the device, the AC coupler comprising: an input end for receiving the wideband signal; an output end for transmitting an output signal; a signal conductor in electrical communication between the input end and the output end, the signal conductor comprising a conductive element and a signal conductor capacitor configured to block direct current (DC) components of the wideband signal while transmitting high-frequency alternating current (AC) components of the wideband signal; and a shielding structure defining a signal return path between the input end and the output end, the shielding structure being configured for conducting at least the AC components of the wideband signal in the signal return path, wherein: the signal conductor has a signal conductor width; the shielding structure has a width substantially greater than the signal conductor width to confine electric fields and currents in the shielding structure substantially to a region proximate to the signal conductor; and the signal conductor and the shielding structure are arranged as a transmission line.

2. An AC coupler for transmitting high-frequency components of a wideband signal, the device, the AC coupler comprising: an input end for receiving the wideband signal; an output end for transmitting an output signal; a signal conductor in electrical communication between the input end and the output end, the signal conductor comprising a conductive element and a signal conductor capacitor configured to block direct current (DC) components of the wideband signal while transmitting high-frequency alternating current (AC) components of the wideband signal; and a shielding structure defining a signal return path between the input end and the output end, the shielding structure being configured for conducting at least the AC components of the wideband signal in the signal return path, wherein: the signal conductor has a signal conductor width; the shielding structure has a width substantially greater than the signal conductor width; the shielding structure is spaced from the signal conductor by an offset distance orthogonal to the width of the shielding structure; the difference between the width of the shielding structure and the signal conductor width is substantially greater than the offset distance; and the signal conductor and the shielding structure are arranged as a transmission line.

3. The AC coupler of embodiment 2, wherein the width of the shielding structure exceeds the signal conductor width by at least 2 times the offset distance, or the width of the shielding structure exceeds the signal conductor width by 2 to 10 times the offset distance.

4. The AC coupler of any of embodiments 1 to 3, wherein: the shielding structure comprises a shielding structure conductive element; and the width of the shielding structure is defined by a width of the shielding structure conductive element.

5. The AC coupler of any of embodiments 1 to 3, wherein: the shielding structure comprises a shielding structure conductive element and a shielding structure capacitor; and the width of the shielding structure is defined by a width of at least one of the shielding structure conductive element and the shielding structure capacitor.

6. The AC coupler of any of embodiments 1 to 5, wherein the width of the shielding structure is at least 1.5 times the signal conductor width, or the width of the shielding structure is in a range of 1.5 to 6 times the signal conductor width.

7. The AC coupler of any of embodiments 1 to 6, wherein the width of the signal conductor is defined by a width of the signal conductor capacitor.

8. The AC coupler of embodiment 1, wherein the shielding structure is spaced from the signal conductor by an offset distance orthogonal to the width of the shielding structure, and the difference between the width of the shielding structure and the signal conductor width is substantially greater than the offset distance.

9. The AC coupler of embodiment 8, wherein the width of the shielding structure exceeds the signal conductor width by at least 2 times the offset distance, or the width of the shielding structure exceeds the signal conductor width by 2 to 10 times greater than the offset distance.

10. The AC coupler of embodiment 1, wherein the signal conductor and the shielding structure are arranged in a microstrip configuration, a stripline configuration, or a coaxial configuration.

11. The AC coupler of embodiment 1, wherein the shielding structure comprises a first shielding structure and a second shielding structure, and the signal conductor is positioned between the first shielding structure and the second shielding structure.

12. The AC coupler of embodiment 11, wherein: the signal conductor is positioned between the first shielding structure and the second shielding structure along a first axis; the shielding structure comprises a third shielding structure and a fourth shielding structure; and the signal conductor is positioned between the third shielding structure and the fourth shielding structure along a second axis orthogonal to the first axis, such that the first shielding structure, the second shielding structure, the third shielding structure, and the fourth shielding structure collectively surround the signal conductor.

13. The AC coupler of embodiment 12, comprising a dielectric substrate supporting the signal conductor, wherein: the third shielding structure comprises at least two capacitors spaced by a first gap; the fourth shielding structure comprises at least two capacitors spaced by a second gap; and the dielectric substrate extends into the first gap and into the second gap.

14. The AC coupler of embodiment 1, wherein the shielding structure surrounds the signal conductor.

15. The AC coupler of embodiment 1, wherein the signal conductor is a first signal conductor and the signal conductor capacitor is a first signal conductor capacitor, and further comprising a second signal conductor in electrical communication between the input end and the output end, wherein: the second signal conductor comprises a second signal conductor capacitor; the second signal conductor capacitor is coplanar with the first signal conductor capacitor and is spaced from the first signal conductor capacitor by a gap; and the signal conductor width is defined by a sum of a width of the first signal conductor capacitor, a width of the second signal conductor capacitor, and the gap.

16. The AC coupler of embodiment 15, comprising a dielectric substrate supporting the first signal conductor capacitor and the second signal conductor capacitor.

17. The AC coupler of embodiment 1, wherein the signal conductor is a first signal conductor and the signal conductor capacitor is a first signal conductor capacitor, and further comprising a second signal conductor in electrical communication between the input end and the output end, wherein: the first signal conductor and the second signal conductor extend between the input end and the output end along a longitudinal axis; the second signal conductor comprises a second signal conductor capacitor; the second signal conductor capacitor is spaced from the first signal conductor capacitor by a gap along a transverse axis orthogonal to the longitudinal axis; and the signal conductor width is defined by a width of the first signal conductor capacitor or a width of the second signal conductor capacitor.

18. The AC coupler of embodiment 17, comprising a first dielectric substrate supporting the first signal conductor capacitor and a second dielectric substrate supporting the second signal conductor capacitor.

19. The AC coupler of any of embodiments 1 to 18, comprising a dielectric substrate supporting the signal conductor.

20. The AC coupler of embodiment 19, comprising another dielectric substrate supporting the shielding structure.

21. The AC coupler of embodiment 19, wherein the dielectric substrate has a thickness and comprises an opening extending through at least a portion of the thickness, and the signal conductor capacitor is positioned in the opening.

22. The AC coupler of embodiment 21, wherein the signal conductor capacitor has a thickness substantially the same as the thickness of the dielectric substrate.

23. The AC coupler of embodiment 21 or 22, wherein the signal conductor capacitor has a width in a direction orthogonal to the thickness of the dielectric substrate, and the opening has a width in a range of 150 to 500% (or 1.5 to 5 times) of the width of the signal conductor capacitor.

24. The AC coupler of embodiment 19, wherein the signal conductor capacitor is substantially coplanar with the dielectric substrate.

25. The AC coupler of any of embodiments 1 to 24, wherein the conductive element has a width substantially the same as the signal conductor width.

26. The AC coupler of any of embodiments 1 to 25, wherein the conductive element comprises a plurality of conductive elements, and the signal conductor capacitor comprises a plurality of signal conductor capacitors interconnected by the plurality of conductive elements.

27. The AC coupler of embodiment 26, wherein the plurality of signal conductor capacitors comprises series-connected capacitors, parallel-connected capacitors, or both series-connected capacitors and parallel-connected capacitors.

28. The AC coupler of embodiment 26, wherein at least some of the plurality of signal conductor capacitors are series-connected capacitors, and the signal conductor further comprises a plurality of resistors disposed in shunt relation to the series-connected capacitors for equalizing DC voltages across the series-connected capacitors.

29. The AC coupler of any of embodiments 1 to 28, comprising a dielectric substrate, wherein the signal conductor capacitor comprises one or more pairs of capacitors, and the capacitors of each pair are respectively positioned on opposite sides of the dielectric substrate.

30. The AC coupler of any of embodiments 1 to 28, comprising a dielectric substrate, wherein: the dielectric substrate comprises first side and an opposing second side; the signal conductor capacitor comprises an array of first capacitors positioned on the first side and spaced from each other by respective intervening regions, and an array of second capacitors positioned on the second side and spaced from each other by respective intervening regions; each first capacitor extends to a first capacitor height relative to the first side, and each second capacitor extends to a second capacitor height relative to the second side; and the AC coupler further comprises a plurality of filler structures respectively positioned in the intervening regions, wherein each filler structure fills in the corresponding intervening region between adjacent first capacitors or second capacitors, and each filler structure has a height substantially matching the first capacitor height or the second capacitor height.

31. The AC coupler of embodiment 30, wherein the filler structures comprise conductive materials, dielectric materials, or both conductive materials and dielectric materials.

32. The AC coupler of any of embodiments 1 to 31, wherein the input end and the output end comprise respective AC connectors, and each AC connector comprises an inner conductor communicating with the signal conductor and an outer shield communicating with the shielding structure.

33. The AC coupler of embodiment 32, wherein the inner conductors and the signal conductor capacitor are generally aligned along a common axis.

34. The AC coupler of embodiment 32 or 33, wherein the outer shields have respective inside diameters, and the signal conductor capacitor has a width less than the inside diameters.

35. The AC coupler of any of embodiments 1 to 34, wherein the shielding structure comprises a shielding structure conductive element and a shielding structure capacitor.

36. The AC coupler of embodiment 35, wherein the shielding structure conductive element comprises a plurality of shielding structure conductive elements, and the shielding structure capacitor comprises a plurality of shielding structure capacitors interconnected by the plurality of shielding structure conductive elements.

37. The AC coupler of embodiment 36, wherein the plurality of shielding structure capacitors comprises series-connected capacitors, parallel-connected capacitors, or both series-connected capacitors and parallel-connected capacitors.

38. The AC coupler of embodiment 36, wherein at least some of the plurality of shielding structure capacitors are series-connected shielding structure capacitors, and the shielding structure further comprises a plurality of resistors disposed in shunt relation to the series-connected shielding structure capacitors for equalizing DC voltages across the series-connected shielding structure capacitors.

39. The AC coupler of embodiment 38, comprising a dielectric substrate supporting the shielding structure, wherein the shielding structure capacitors are positioned on a side of the dielectric substrate facing the signal conductor, and the resistors are positioned on an opposite side of the dielectric substrate.

40. The AC coupler of any of embodiments 36 to 39, wherein the shielding structure comprises a longitudinal axis extending generally from the input end to the output end, and the plurality of shielding structure capacitors comprises one or more sets of capacitors, and the capacitors of each set are spaced from each other along a direction transverse to the longitudinal axis.

41. The AC coupler of any of embodiments 35 to 40, comprising a dielectric substrate supporting the shielding structure, wherein the shielding structure capacitor is positioned on a side of the dielectric substrate facing the signal conductor.

42. The AC coupler of any of embodiments 1 to 41, comprising a mechanism configured to adjust a characteristic impedance of the transmission line.

43. The AC coupler of embodiment 42, wherein the mechanism is configured to move the shielding structure relative to the signal conductor.

44. The AC coupler of embodiment 43, wherein the mechanism comprises a plate having a slot, and the shielding structure is movable along the slot or is coupled to an adjustment member that is movable along the slot.

45. The AC coupler of any of embodiments 1 to 44, wherein at least one of the signal conductor and the shielding structure comprises a first end proximate to the input end and a second end proximate to the output end, and the first end and the second end comprise respective structural transitions configured to minimize signal reflections.

46. The AC coupler of embodiment 45, wherein the structural transitions have a tapered or stepped geometry.

47. The AC coupler of any of embodiments 1 to 46, comprising a dielectric substrate supporting the signal conductor, wherein the dielectric substrate comprises a first end spaced from the input end by a first gap and a second end spaced from the output end by a second gap.

48. The AC coupler of any of embodiments 1 to 47, wherein the dielectric substrate comprises a plurality of geometric features configured to increase leakage current path lengths.

49. The AC coupler of embodiment 48, wherein the geometric features are arranged in a repeating pattern between the input end and the output end.

50. The AC coupler of embodiment 48 or 49, wherein the geometric features comprise openings, raised features, or both openings and raised features.

51. The AC coupler of any of embodiments 1 to 50, wherein at least one of the signal conductor capacitor and the shielding structure capacitor is a leadless multilayer capacitor.

52. A spectrometer, comprising: the AC coupler of any of embodiments 1 to 51; and an ion detector communicating with the input end.

53. The spectrometer of embodiment 52, comprising an ion analyzer communicating with the ion detector.

54. The spectrometer of embodiment 53, wherein the ion analyzer comprises a mass analyzer, an ion mobility drift cell, or both a mass analyzer and an ion mobility drift cell.

55. The spectrometer of any of embodiment 52 to 54, comprising a data acquisition system communicating with the output end.

56. A method for making an AC coupler, the method comprising: arranging a signal conductor and a shielding structure as a transmission line configured for transmitting high-frequency components of a wideband signal from an input connector to an output connector, wherein: the signal conductor is configured for being interconnected between respective center conductors of the input connector and the output connector, and the signal conductor comprises a conductive element and a capacitor configured to block direct current (DC) components of the wideband signal while transmitting high-frequency alternating current (AC) components of the wideband signal; and the shielding structure is configured for being interconnected between respective shielding conductors of the input connector and the output connector, and for conducting at least the AC components of the wideband signal, and the shielding structure has a width substantially greater than a width of the signal conductor to confine electric fields and currents in the shielding structure substantially to a region proximate to the signal conductor.

57. A method for making an AC coupler, the method comprising: arranging a signal conductor and a shielding structure as a transmission line configured for transmitting high-frequency components of a wideband signal from an input connector to an output connector, wherein: the signal conductor is configured for being interconnected between respective center conductors of the input connector and the output connector, and the signal conductor comprises a conductive element and a capacitor configured to block direct current (DC) components of the wideband signal while transmitting high-frequency alternating current (AC) components of the wideband signal; the shielding structure is configured for being interconnected between respective shielding conductors of the input connector and the output connector, and for conducting at least the AC components of the wideband signal; the shielding structure has a width substantially greater than a width of the signal conductor; the shielding structure is spaced from the signal conductor by an offset distance orthogonal to the width of the shielding structure; and the difference between the width of the shielding structure and the width of the signal conductor is substantially greater than the offset distance.

58. The method of embodiment 56 or 57, comprising supporting the conductive element and the capacitor on a dielectric substrate.

59. The method of embodiment 58, comprising positioning the capacitor in an opening of the dielectric substrate such that the capacitor is substantially coplanar with the dielectric substrate.

It will be understood that the term "in signal communication" or "electrical communication" as used herein means that two or more systems, devices, components, modules, or sub-modules are capable of communicating with each other via signals that travel over some type of signal path. The signals may be communication, power, data, or energy signals, which may communicate information, power, or energy from a first system, device, component, module, or sub-module to a second system, device, component, module, or sub-module along a signal path between the first and second system, device, component, module, or sub-module. The signal paths may include physical, electrical, magnetic, electromagnetic, electrochemical, optical, wired, or wireless connections. The signal paths may also include additional systems, devices, components, modules, or sub-modules between the first and second system, device, component, module, or sub-module.

More generally, terms such as "communicate" and "in . . . communication with" (for example, a first component "communicates with" or "is in communication with" a second component) are used herein to indicate a structural, functional, mechanical, electrical, signal, optical, magnetic, electromagnetic, ionic or fluidic relationship between two or more components or elements, as dictated by the context in which such terms are used. As such, the fact that one component is said to communicate with a second component is not intended to exclude the possibility that additional components may be present between, and/or operatively associated or engaged with, the first and second components.

It will be understood that various aspects or details of the invention may be changed without departing from the scope of the invention. Furthermore, the foregoing description is for the purpose of illustration only, and not for the purpose of limitation—the invention being defined by the claims.

What is claimed is:

1. An AC coupler for transmitting high-frequency components of a wideband signal, the AC coupler comprising:
an input end for receiving the wideband signal;
an output end for transmitting an output signal;
a signal conductor in electrical communication between the input end and the output end, the signal conductor comprising a conductive element and a signal conductor capacitor configured to block direct current (DC) components of the wideband signal on the order of kilovolts or greater while transmitting high-frequency alternating current (AC) components of the wideband signal; and
a shielding structure defining a signal return path between the input end and the output end, the shielding structure being configured for conducting at least the AC components of the wideband signal in the signal return path, wherein:
the signal conductor has a signal conductor width;
the shielding structure has a width substantially greater than the signal conductor width to confine electric fields and currents in the shielding structure substantially to a region proximate to the signal conductor; and
the signal conductor and the shielding structure are arranged as a transmission line.

2. The AC coupler of claim 1, wherein the shielding structure has a configuration selected from the group consisting of:
the shielding structure comprises a shielding structure conductive element, and the width of the shielding structure is defined by a width of the shielding structure conductive element; and
the shielding structure comprises a shielding structure conductive element and a shielding structure capacitor, and the width of the shielding structure is defined by a width of at least one of the shielding structure conductive element and the shielding structure capacitor.

3. The AC coupler of claim 1, wherein the width of the shielding structure is at least 1.5 times the signal conductor width, or the width of the shielding structure is in a range of 1.5 to 6 times the signal conductor width.

4. The AC coupler of claim 1, wherein the width of the signal conductor is defined by a width of the signal conductor capacitor.

5. The AC coupler of claim 1, wherein the shielding structure is spaced from the signal conductor by an offset distance orthogonal to the width of the shielding structure, and the difference between the width of the shielding structure and the signal conductor width is substantially greater than the offset distance.

6. The AC coupler of claim 5, wherein the width of the shielding structure exceeds the signal conductor width by at least 2 times the offset distance, or the width of the shielding structure exceeds the signal conductor width by 2 to 10 times greater than the offset distance.

7. The AC coupler of claim 1, wherein the signal conductor and the shielding structure are arranged according to a configuration selected from the group consisting of:

the signal conductor and the shielding structure are arranged in a microstrip configuration;
the signal conductor and the shielding structure are arranged in a stripline configuration;
the signal conductor and the shielding structure are arranged in a coaxial configuration;
the shielding structure comprises a first shielding structure and a second shielding structure, and the signal conductor is positioned between the first shielding structure and the second shielding structure; and
the shielding structure surrounds the signal conductor.

8. The AC coupler of claim 1, comprising a dielectric substrate supporting the signal conductor or the shielding structure, or a dielectric substrate supporting the signal conductor and another dielectric substrate supporting the shielding structure.

9. The AC coupler of claim 1, comprising a dielectric substrate supporting the signal conductor, wherein the dielectric substrate has a thickness and comprises an opening extending through at least a portion of the thickness, and the signal conductor capacitor is positioned in the opening.

10. The AC coupler of claim 1, comprising a dielectric substrate supporting the signal conductor, wherein the signal conductor capacitor is substantially coplanar with the dielectric substrate.

11. The AC coupler of claim 1, wherein the conductive element has a width substantially the same as the signal conductor width.

12. The AC coupler of claim 1, wherein the conductive element comprises a plurality of conductive elements, and the signal conductor capacitor comprises a plurality of signal conductor capacitors interconnected by the plurality of conductive elements.

13. The AC coupler of claim 1, comprising a dielectric substrate, wherein the signal conductor capacitor comprises one or more pairs of capacitors, and the capacitors of each pair are respectively positioned on opposite sides of the dielectric substrate.

14. The AC coupler of claim 1, wherein the shielding structure has a configuration selected from the group consisting of:
the shielding structure comprises a shielding structure conductive element and a shielding structure capacitor; and
the shielding structure comprises a plurality of shielding structure conductive elements, and a plurality of shielding structure capacitors interconnected by the plurality of shielding structure conductive elements.

15. The AC coupler of claim 1, comprising a mechanism configured to adjust a characteristic impedance of the transmission line.

16. The AC coupler of claim 1, wherein at least one of the signal conductor and the shielding structure comprises a first end proximate to the input end and a second end proximate to the output end, and the first end and the second end comprise respective structural transitions configured to minimize signal reflections.

17. The AC coupler of claim 1, comprising a dielectric substrate supporting the signal conductor, wherein the dielectric substrate comprises a first end spaced from the input end by a first gap and a second end spaced from the output end by a second gap.

18. The AC coupler of claim 1, wherein the dielectric substrate comprises a plurality of geometric features configured to increase leakage current path lengths.

19. A spectrometer, comprising:
the AC coupler of claim 1; and
an ion detector communicating with the input end.

20. A method for making an AC coupler, the method comprising:
arranging a signal conductor and a shielding structure as a transmission line configured for transmitting high-frequency components of a wideband signal from an input connector to an output connector, wherein:
the signal conductor is configured for being interconnected between respective center conductors of the input connector and the output connector, and the signal conductor comprises a conductive element and a capacitor configured to block direct current (DC) components of the wideband signal on the order of kilovolts or greater while transmitting high-frequency alternating current (AC) components of the wideband signal; and
the shielding structure is configured for being interconnected between respective shielding conductors of the input connector and the output connector, and for conducting at least the AC components of the wideband signal, and the shielding structure has a width substantially greater than a width of the signal conductor to confine electric fields and currents in the shielding structure substantially to a region proximate to the signal conductor.

* * * * *

UNITED STATES PATENT AND TRADEMARK OFFICE
CERTIFICATE OF CORRECTION

PATENT NO. : 9,590,583 B2
APPLICATION NO. : 14/753958
DATED : March 7, 2017
INVENTOR(S) : Shahrzad Jalali Mazlouman et al.

It is certified that error appears in the above-identified patent and that said Letters Patent is hereby corrected as shown below:

In the Specification

Column 17, Line 53, delete "10 MSΩ)." and insert -- 10 MΩ). --, therefor.

Signed and Sealed this
Twentieth Day of February, 2018

Andrei Iancu
*Director of the United States Patent and Trademark Office*